(12) United States Patent
McWeeney et al.

(10) Patent No.: US 8,246,689 B2
(45) Date of Patent: *Aug. 21, 2012

(54) URETERAL STENT FOR IMPROVED PATIENT COMFORT

(76) Inventors: John O. McWeeney, Brighton, MA (US); Willet F. Whitmore, III, Sarasota, FL (US); Stephanie Rubin, Falls Church, VA (US)

( * ) Notice: Subject to any disclaimer, the term of this patent is extended or adjusted under 35 U.S.C. 154(b) by 124 days.

This patent is subject to a terminal disclaimer.

(21) Appl. No.: 12/698,487

(22) Filed: Feb. 2, 2010

(65) Prior Publication Data
US 2010/0198358 A1 Aug. 5, 2010

Related U.S. Application Data

(63) Continuation of application No. 11/327,409, filed on Jan. 9, 2006, now Pat. No. 7,678,154, which is a continuation of application No. 10/406,876, filed on Apr. 4, 2003, now Pat. No. 6,991,614, which is a continuation-in-part of application No. 09/849,202, filed on May 4, 2001, now Pat. No. 6,676,623, which is a continuation-in-part of application No. 09/300,657, filed on Apr. 27, 1999, now Pat. No. 6,656,146, which is a continuation of application No. 08/743,885, filed on Nov. 6, 1996, now Pat. No. 6,849,069.

(60) Provisional application No. 60/006,259, filed on Nov. 7, 1995, provisional application No. 60/009,983, filed on Jan. 16, 1996, provisional application No. 60/025,284, filed on Sep. 19, 1996.

(51) Int. Cl.
*A61F 2/04* (2006.01)
(52) U.S. Cl. ..................... 623/23.66; 623/23.7
(58) Field of Classification Search .................. 623/23.7, 623/23.64–23.66
See application file for complete search history.

(56) References Cited

U.S. PATENT DOCUMENTS
4,307,723 A 12/1981 Finney
(Continued)

FOREIGN PATENT DOCUMENTS
DE 3517813 A1 11/1986
(Continued)

OTHER PUBLICATIONS

Extended European Search Report for European Application No. 10184665.7, mailed on Jan. 24, 2011, 4 pages.
(Continued)

*Primary Examiner* — Theodore Stigell

(57) ABSTRACT

A ureteral stent for assisting the movement of urine along a patient's ureter and into the patient's bladder. The stent includes an elongated tubular segment extending toward the bladder from a kidney end region for placement in the renal cavity to a bladder end region. A central lumen connects at least one opening at the first end region to at least one opening in the bladder end region. Thin flexible tail(s) are attached to the bladder end region of the tubular segment at a point outside the bladder so as to receive urine from the opening in the bladder end region of the tubular segment and to transport urine from there across the ureter/bladder junction and into the bladder. The tails include an elongated external urine-transport surface sized and configured to transport urine along the ureter. The urine transporting surface(s) are sized and configured to extend along at least part of the ureter, across the ureter/bladder junction, and from there into the bladder. In some embodiments, the distal region includes a tubular body with a lumen in fluid communication with an interstitial area defined by one or more flexible filaments of the proximal region forming at least one loop.

21 Claims, 18 Drawing Sheets

U.S. PATENT DOCUMENTS

| | | | | |
|---|---|---|---|---|
| 4,671,795 A * | 6/1987 | Mulchin | | 604/530 |
| 4,913,683 A | 4/1990 | Gregory | | |
| 6,676,623 B2 * | 1/2004 | Whitmore, III | | 604/8 |
| 6,991,614 B2 * | 1/2006 | McWeeney et al. | | 604/8 |

FOREIGN PATENT DOCUMENTS

| | | |
|---|---|---|
| DE | 3740288 C1 | 4/1989 |
| DE | 4103573 A1 | 8/1992 |
| DE | 4134030 A1 | 4/1993 |
| EP | 0326908 A2 | 8/1989 |

OTHER PUBLICATIONS

Notice of Allowance for U.S. Appl. No. 08/743,885, mailed on Mar. 16, 1999, 4 pages.

Office Action for U.S. Appl. No. 08/743,885, mailed on Nov. 9, 2001, 7 pages.

Office Action for U.S. Appl. No. 08/743,885, mailed on May 8, 2001, 8 pages.

Office Action for U.S. Appl. No. 08/743,885, mailed on Feb. 17, 1999, 4 pages.

Office Action for U.S. Appl. No. 08/743,885, mailed on Jul. 5, 2000, 5 pages.

Supplemental Notice of Allowability for U.S. Appl. No. 08/743,885, mailed on Aug. 3, 1999, 2 pages.

Notice of Allowance for U.S. Appl. No. 08/743,885, mailed on Jul. 25, 2002, 4 pages.

Office Action for U.S. Appl. No. 09/849,202, mailed on Jun. 17, 2003, 7 pages.

Office Action for U.S. Appl. No. 08/743,885, mailed on Apr. 24, 2002, 10 pages.

Office Action for U.S. Appl. No. 09/849,202, mailed on Jan. 22, 2003, 10 pages.

Supplemental Notice of Allowability for U.S. Appl. No. 09/300,657, mailed on Sep. 16, 2003, 15 pages.

Office Action for U.S. Appl. No. 09/849,202, mailed on Sep. 30, 2002, 13 pages.

Notice of Allowance for U.S. Appl. No. 09/849,202, mailed on Aug. 25, 2003, 6 pages.

Office Action for U.S. Appl. No. 09/300,657, mailed on Aug. 16, 2000, 10 pages.

Notice of Allowance for U.S. Appl. No. 09/300,657, mailed on Jun. 17, 2003, 13 pages.

Office Action for U.S. Appl. No. 09/300,657, mailed on May 23, 2001, 9 pages.

Office Action for U.S. Appl. No. 09/300,657, mailed on Mar. 24, 2003, 8 pages.

Office Action for U.S. Appl. No. 09/300,657, mailed on Oct. 23, 2001, 6 pages.

Office Action for U.S. Appl. No. 09/300,657, mailed on Aug. 28, 2002, 8 pages.

Office Action for U.S. Appl. No. 09/300,657, mailed on May 9, 2002, 8 pages.

Office Action for EP Application No. 10184665.7, mailed Nov. 25, 2011, 3 pages.

Office Action Response for EP Application No. 10184665.7, filed Mar. 14, 2012, 4 pages.

\* cited by examiner

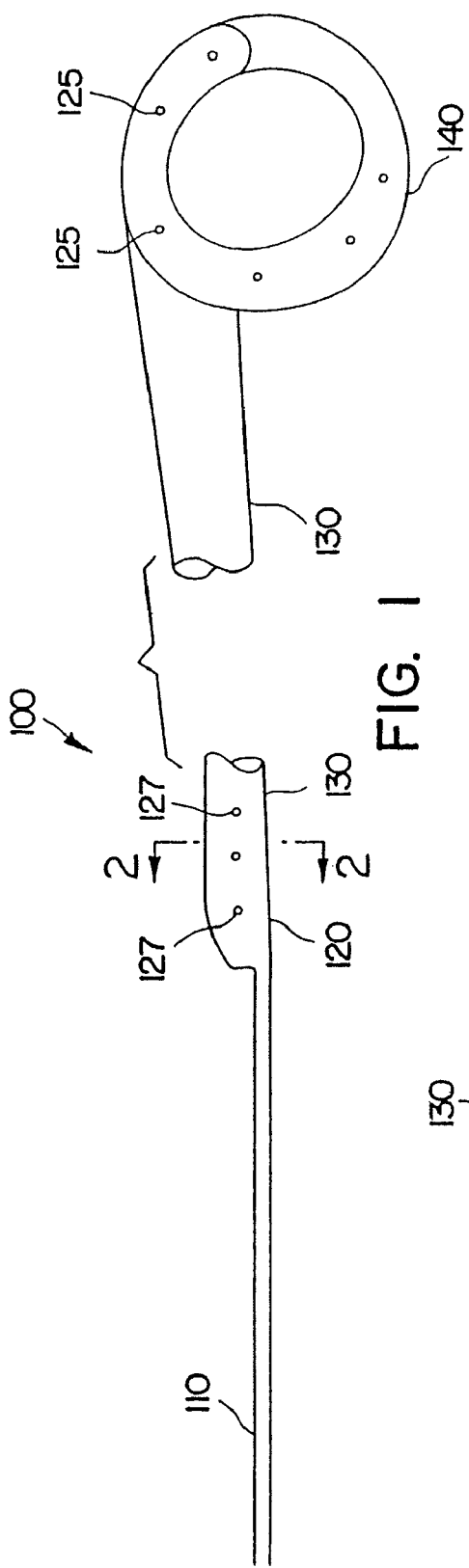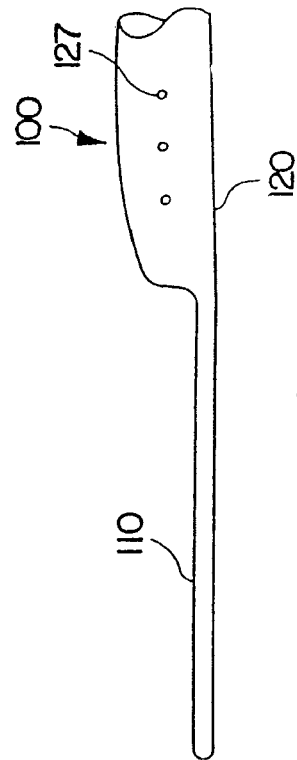

FIG. 13
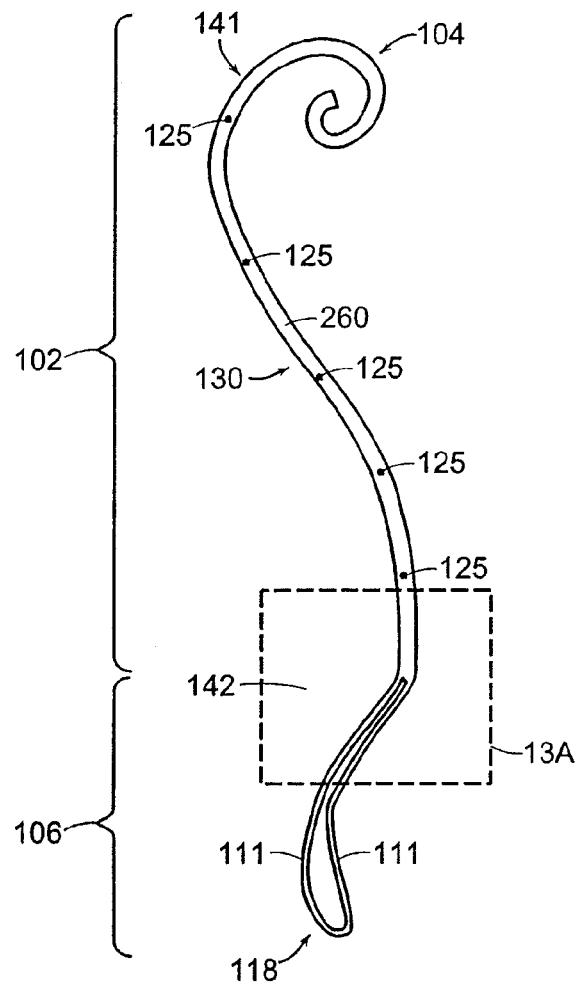
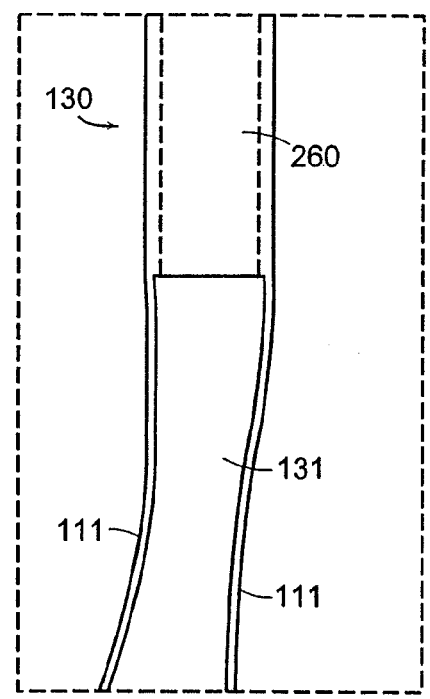
FIG. 13A

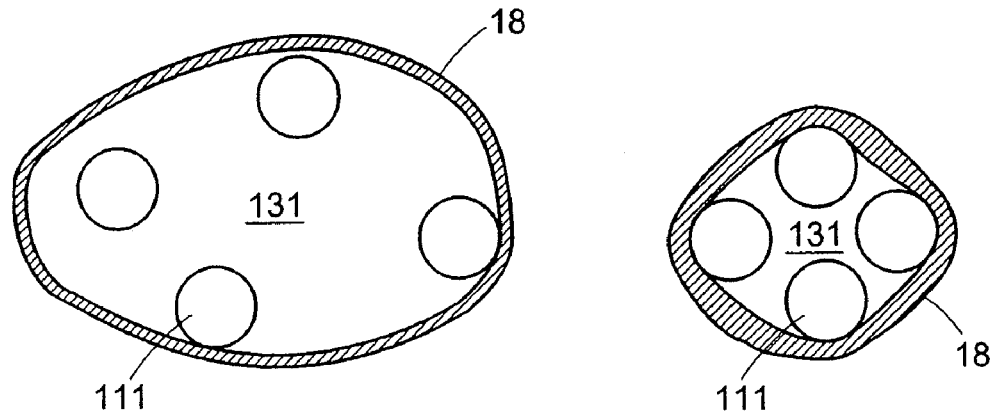
FIG. 15B    FIG. 15C
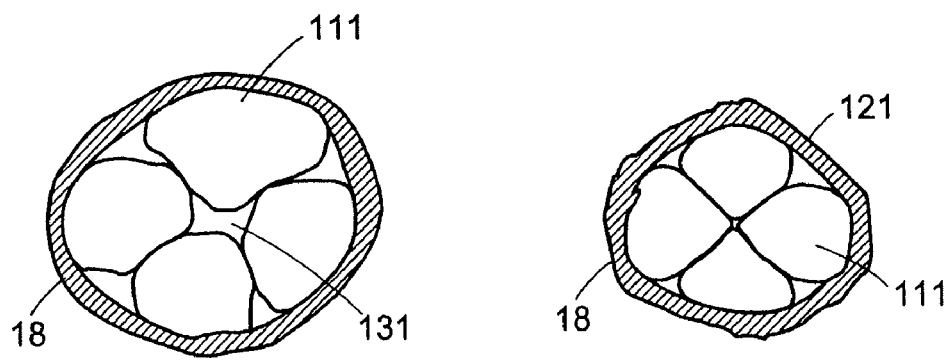
FIG. 15C'    FIG. 15C"

URETERAL STENT FOR IMPROVED PATIENT COMFORT

RELATED APPLICATIONS

This application is a continuation of U.S. patent application Ser. No. 11/327,409, filed Jan. 9, 2006 now U.S. Pat. No. 7,678,154, entitled "Ureteral Stent for Improved Patient Comfort," which is a continuation of U.S. patent application Ser. No. 10/406,876, filed Apr. 4, 2003, entitled "Ureteral Stent for Improved Patient Care," now U.S. Pat. No. 6,991,614, which is a continuation-in-part of U.S. patent application Ser. No. 09/849,202, filed May 4, 2001, now U.S. Pat. No. 6,676,623, and which is a continuation-in-part of U.S. patent application Ser. No. 09/300,657, filed on Apr. 27, 1999, now U.S. Pat. No. 6,656,146, which is a continuation of U.S. patent application Ser. No. 08/743,885, filed on Nov. 6, 1996, now U.S. Pat. No. 6,849,069, which claims priority to and the benefit of U.S. Provisional Patent Application Ser. No. 60/006,259 filed Nov. 7, 1995, U.S. Provisional Patent Application Ser. No. 60/009,983, filed Jan. 16, 1996 and U.S. Provisional Patent Application Ser. No. 60/025,284 filed Sep. 19, 1996, the contents of each of these applications are incorporated herein by reference in their entirety.

TECHNICAL FIELD

This application relates generally to medical devices for drainage of fluids, and more specifically to ureteral stents.

BACKGROUND

Ureteral stents are used to assist urinary drainage from the kidney to the bladder in patients with ureteral obstruction or injury, or to protect the integrity of the ureter in a variety of surgical manipulations. More specifically, stents may be used to treat or avoid ureter obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter.

Ureteral stents typically are tubular in shape, terminating in two opposing ends: a kidney (upper) end and a bladder (lower) end. The ends may be coiled in a pigtail or J-shape to prevent the upward or downward migration of the stent, e.g., with physiological movements. A kidney coil can function as a distal retention structure, designed to retain the stent within the renal pelvis of the kidney and to prevent stent migration down the ureter. The bladder coil sits in the bladder and is designed to prevent stent migration upward toward the kidney. The bladder coil is also used to aid in retrieval and removal of the stent.

Ureteral stents, particularly the portion positioned in the ureter near the bladder and inside the bladder, may produce adverse effects including blood in the urine, a continual urge to urinate, strangury, and flank pain accompanying reflux of urine up the stent (e.g., when voiding) as pressure within the bladder is transmitted to the kidney. In short, stents may cause or contribute to significant patient discomfort and serious medical problems.

FIG. 10 is a schematic drawing of the human urinary tract without a stent, showing the renal pelvis 19, the kidney 23, the ureter 24, and the ureteral orifices 18 opening into the bladder 20. FIG. 11 depicts a typical double-J stent 10 which comprises a small tube 12 which sits inside the urinary system and assists the flow of urine from the kidney (renal pelvis) to the bladder. FIG. 12 depicts prior art indwelling ureteral stent 10 in position. Such stents are typically made of biocompatible plastic, coated plastic, or silicone material. Tube 12 typically varies in size from 4-8 F, and it has multiple small holes throughout its length. A coiled shape pre-formed at each end (distal end 14 and proximal end 16) of the stent 10 is designed to confine its movement within the urinary system, so that it will be maintained in the desired position. The upper (kidney) end (the distal end 14) of the stent can include a distal retention structure 104. The distal end 14 may be closed or tapered, depending on the method of insertion (e.g., the use of a guidewire). The tubular stent extends through the ureteral orifice 18a and into the bladder, fixing orifice 18a open, and thereby enhancing the opportunity for reflux. For clarity, the ureter entering bladder 20 through orifice 18b is not shown. A monofilament thread 22 may be attached to the bladder end of the stent for removal, usually without cystoendoscopy.

U.S. Pat. No. 4,531,933 ("the '933 patent") discloses a ureteral stent having helical coils at each end which are provided for preventing migration and expulsion.

SUMMARY OF THE INVENTION

We have discovered a ureteral stent design that avoids patient discomfort and urine reflux upward toward the kidney. Rather than rely on a tubular structure to contain and facilitate all (or, in some embodiments, any) urine flow along the ureter, the invention features a thin, flexible elongated tail member having an elongated external urine-transport surface. Urine flows along the outside surface of the structure, between that surface and the inside wall of the ureter. Without limiting ourselves to a specific mechanism, it appears that urine may remain attached to, and flow along, the external urine transport surface. The use of a foreign body that is as small as possible in the lower (bladder) end of the ureter and in the bladder itself decreases patient discomfort. Typically, the external urine transport surface is sized and configured to extend along at least part of the ureter near the bladder, across the ureter/bladder junction, and from there through the ureteral opening into the bladder.

While most or all of the length of the stent may rely on such an external surface to assist flow, more typically the stent will also include an upper elongated tubular segment to transport urine along a significant portion of the upper ureter. The upper tubular segment is connected at its lower end to an elongated tail that has the above-described external urine-transport surface. The upper tubular segment comprises: a) an upper region having at least a first opening; b) a lower region having at least a second opening to be positioned in the ureter outside the bladder, and c) a central lumen connecting the first opening to the second opening. The elongated tail is a thin flexible tail member or filament(s) extending from the lower region of the tubular segment at a point outside the bladder so as to receive urine from the second opening of the tubular segment and to transport urine along the ureter from the lower region of the tubular segment across the ureterlbladder junction and into the bladder. Typically, but not exclusively, the upper region of the tubular segment is configured and sized for placement in the renal cavity.

The elongated tail member can include at least one (and more preferably at least two) thread filaments(s). Two or more of the filaments may be configured in at least one filament loop, and, advantageously, the tail comprises no unlooped filaments, so that the tail is free from loose ends. The loop(s) can be made by joining the ends of a single filament, in which case the filament loop comprises a junction of individual filament ends, which junction typically is positioned at the point where tail joins to the elongated tubular segment. Preferably, the tail is long enough to effectively prevent migration of the entire tail into the ureter, and the tail has a smaller outer diameter than the outer diameter of the tubular segment.

The tubular stent segment can be stiff enough to avoid crimping during insertion through the ureter, so that it can be inserted by typical procedures. The tail, on the other hand, can be extremely flexible (soft) in comparison to the tubular segment, and it can have a much smaller diameter than the tubular segment, to avoid discomfort. Even quite thin structures can provide urine transport, and the thinner and more flexible the tail is, the less likely it is to cause patient discomfort. On the other hand, the tail (and its connection to the rest of the stent) should have sufficient strength so the stent can be retrieved by locating the tail in the bladder and pulling on the tail to retrieve the stent from the kidney and ureter. Details of the tail size are discussed below. The use of reinforcing materials (e.g., sutures as described below) permits the use of thinner tails while still providing the ability to locate the tail in the bladder and to retrieve the stent. The tail may be a suture, and the suture may be coated to avoid encrusting.

The external urine-transport surface of the tail can be convex (circular or oval in section), concave, or flat. The tail filament may be fluted. The tail can include an accurately shaped anchor segment to control migration up the ureter. The tail may be either solid or hollow; even when hollow; it is not designed to transport a significant amount of urine internally. The tail may also be tapered.

The upper region of the tubular segment may have a portion designed for placement in the renal cavity, which portion can have an enlarged diameter and/or straight sides and corners. The stent may include an extractor thread attached to the lower end of the elongated tail member.

To make the stent, the tail may be molded in one piece with the tubular segment, or it may be made separately and attached to the bladder end region of the tubular segment at a point toward the kidney from the bladder end of the lower region of the tubular segment. In one embodiment, the tail can be attached near or at the bladder end of the bladder end region of the tubular segment. The stent may include a suture securing the tail to the tubular segment, and the suture may be incorporated into the tail to impart strength to the tail so the tail may be used to retrieve the stent. If the tail includes a hollow lumen, the suture may be positioned inside that lumen. The suture may be attached to the tubular segment at a point in the bladder end region of the tubular segment, and the suture may extend from the point of attachment through an opening in the bladder end region to the central lumen of the tubular segment and from there to the hollow tail. Alternatively, at least the bladder end region of the tubular segment may include two lumens, a main urine-transporting lumen, and a bladder lumen to encase the suture, so that the suture does not become encrusted.

The outer diameter of the tubular segment can be tapered so that it decreases approaching its lower region. The lower region of the tubular segment may include multiple openings positioned, e.g., axially along include its length or radially around its circumference, or in other patterns. In addition, the outer diameter of the stent's tubular segment may decrease approaching the upper region. In other words, the maximum diameter may be at the site of the injury to encourage a sufficiently large inner diameter in the repaired structure, and the tubular segment's outer diameter may decrease moving away from that point of maximum diameter to sections of the normal ureter that are not in need of a broad support structure. Generally, the outer diameter of the upper end of the tubular segment will be greater than the other diameter of the bladder end. The upper region may include multiple openings (inlets).

In an alternative embodiment, the elongated external urine-transport surface is a continuous surface extending from the kidney to the bladder, e.g., it is the outer surface of a solid member extending from the kidney to the bladder.

Another aspect of the invention features a method of introducing a ureteral stent (described above) into a patient, by (a) positioning the kidney end region of the tubular segment within the renal pelvis; and (b) positioning the elongated flexible member(s) in the bladder.

Yet another aspect of the invention features a method of manufacturing a ureteral stent as described above. The method comprises: (a) providing a polymer perform having a tubular shape; (b) forming an elongated tubular stent segment from the polymer pre-form, and (c) providing tail member(s) at an end region of the tubular segment.

Another aspect of the invention relates to a ureteral stent comprising a distal region that includes a tubular body defining a lumen, and a distal retention structure. The distal retention structure maintains a position of the ureteral stent within the body with respect to a kidney. The ureteral stent also includes a proximal region in fluid communication with the distal region and including a distal portion that includes a junction with the distal region. The proximal region can comprise a pliable portion disposable within a ureteral orifice and in communication with the distal portion. The pliable portion is compressible upon the exertion of a body pressure, such as a pressure exerted by the ureteral orifice. The proximal region can also include a proximal portion that comprises one or more flexible filaments. The filament(s) form at least one loop that has a length sufficient to remain within the bladder when the distal retention structure is positioned within the kidney, but the length is insufficient to allow the loop to substantially contact the urethra.

Embodiments of this aspect of the invention include filaments that have a retention force insufficient to maintain the ureteral stent within the bladder. The pliable portion of the stent can extend distally from the ureteral orifice about 3 centimeters or more, and the pliable portion can include a soft section of tube or soft section of the stent compared to other sections of the stent, that is compressible by body pressure. In some embodiments the pliable portion includes a distal end of the plurality of the filaments. Upon exertion of the pressure, the pliable portion can collapse sufficiently to inhibit urine reflux.

Other embodiments include filaments that are sufficiently resilient to provide drainage (e.g., of urine) through an interstitial space. The interstitial space can be defined by the filaments and can be in fluid communication with the lumen of the distal region. The interstitial space, can be at least partially collapsible by body pressure. An embodiment includes at least one loop that is formed from a continuous filament. Two or more loops can be formed, and each loop can be formed from a single filament.

In other embodiments, the pliable portion can include a distal end of the filaments, and the filaments can be configured to minimize any sharp edges at the junction. The proximal region can be integrally formed with the distal region, and the distal region can have a hardness that is greater than the hardness of the proximal region. In some embodiments the hardness of the stent gradually decreases from a distal location of the distal region to a proximal location of the proximal region. The distal region typically has a hardness value of at least about 80-110 Shore A, although some embodiments can include a distal region with a hardness of about 60-80 Shore A. The proximal region can have a hardness of about 60-80 Shore A.

The length of loops formed by the filament(s) can be sufficient to maintain at least a portion of the stent within the bladder after intubation of the stent, including upon routine movement of the kidney and the bladder. The filaments can also have sufficient tensile strength to provide for extubation of the stent via the bladder or urethra. The ureteral stent can include a lubricious coating, and the tubular body of the stent can include one or more openings disposed along its length.

Another aspect of the invention relates to a ureteral stent comprising a distal region that includes a tubular body defining a lumen, and a distal retention structure. The distal retention structure maintains a position of the ureteral stent within the body. The stent also includes a proximal region in communication with the distal region. A portion of the proximal region is disposable within a ureteral orifice and includes a plurality of flexible filaments compressible upon the exertion of a body pressure, such as by a ureteral orifice. The filaments form at least one loop and have a length sufficient to remain within the bladder when the distal retention structure is positioned within the kidney, but the length is insufficient to allow the loop to substantially contact the prostatic urethra.

Yet another aspect of the invention features a medical device comprising a distal region that includes a tubular body defining a longitudinal axis and at least one lumen, the distal region including a distal retention structure. The medical device also includes a proximal region in fluid communication with the distal region, the proximal region comprising a distal portion and a proximal portion. The proximal portion includes at least two filaments forming at least two loops that define an interstitial space. The interstitial space is in fluid communication with the lumen. The loops are flexible, such that a pressure of the body can compress the interstitial space. The medical device has a hardness that gradually decreases from a distal location of the distal region to a proximal location of the proximal region.

As described in greater detail below, the stent may be manufactured from a polymer form having a tubular shape by forcing the form onto a mandrel to produce the desired three-dimensional shape (coils, etc.). The elongated tail member(s) or filament(s) can be attached to one end of the tubular member(s) using sutures as described above. Heat treatments to fuse the structures and/or standard adhesives may be used. Alternatively, the tubular member(s) and the elongated member or filament(s) can be integrally formed, constituting a one-piece stent.

The use of relatively thin, flexible elongated member(s) or filament(s) to assist urine flow across the uretero-vesical junction and into the bladder may reduce reflux and irritation, thereby reducing patient discomfort and medical problems associated with other types of ureteral stents.

Other features and advantages of the invention will appear from the following description of the preferred embodiment, and from the claims.

BRIEF DESCRIPTION OF THE DRAWINGS

FIG. 1 is a side view of a ureteral stent with a central portion of the tubular segment omitted.

FIG. 2 is a cross-sectional view along line 2-2 in FIG. 1.

FIG. 3 is an enlarged side-view of a portion of the ureteral stent in FIG. 1.

FIG. 13 illustrates an embodiment of a ureteral stent of the invention comprising a proximal region including a loop formed from one or more flexible filament(s).

FIG. 13A is an exploded view of a portion of the embodiment of a ureteral stent shown at 13A in FIG. 13.

DETAILED DESCRIPTION

Figure 4A:
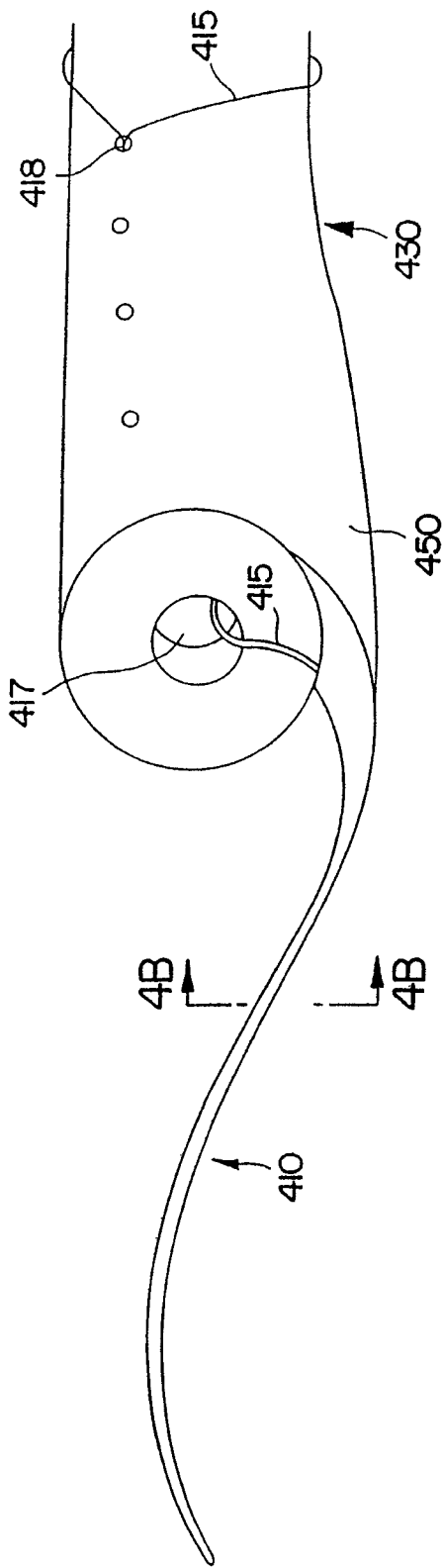
FIG. 4A is a view of an alternate embodiment of the stent in FIG. 1.

In FIG. 1, ureteral stent 100 includes an elongated tubular body 130 connecting coil end 140 to straight end region 120. Tubular body 130 is designed to extend from the renal pelvis through the ureter to a terminus upstream of the bladder. Tail 11 0 is attached to straight end region 120, and tail 110 extends along the ureter, across the ureter/bladder junction and into the bladder.

The two opposing end regions 120 and 140 of elongated tubular body 130 are illustrated in FIG. 1. Coiled end region 140 is designed to be placed in the renal pelvis of the kidney. For illustrative purposes, coiled end region 140 is shown with a pigtail helical coil although any shape that will retain the stent in place within the kidney will do. Coiled end region 140 includes several openings 125 placed along the wall of the tubular body; the openings may be arranged in various geometries (e.g., axial, circumferential, spiral). The entire tubular segment, including the region between the kidney and the bladder end regions, may include additional openings.

The bladder end region 120 of the tubular stent segment is designed to terminate in the ureter, upstream of the bladder. For purposes of further description, the end region of stent 100 received in the kidney will be designated the kidney end and the opposite end of stent 100 toward the bladder will be termed the bladder end.

FIG. 2 is a cross-sectional view of stent 100 of FIG. 1. In FIG. 2, elongated tubular body 130 has annular walls 250 having an inner and outer diameter. The outer diameter of tubular body 130 may be substantially uniform throughout much of the length of the tube, or it may taper from a relatively short region of larger diameter (the site of the repair, where there is a risk that the healing process will substantially restrict flow in the lumen) to a region of generally small diameter. The precise configuration may depend on the ureteral defect being corrected. Just one of the many classes of procedures that can benefit from the stent are endopyelotomies—procedures for treating ureteropelvic junction (UPJ) obstruction by an incision which perforates the ureter at the stricture. In these and other procedures, the stent keeps the ureter lumen open during the healing process, so that the inner diameter of the resulting healed structure is adequate. The section of the tubular segment at the defect is large enough to support growth of repair tissue having an adequate inner diameter. At other sections of the ureter (e.g., sections not being surgically repaired), the outer diameter of the tubular segment may be far smaller, but with an inner diameter adequate for passage over a guidewire. For example, the outer diameter of the bladder end region of the tubular segment typically is 2 F-12 F. Preferably the outer diameter of tubular body 130 is greatest at the ureteropelvic junction obstruction but begins to taper approaching each end. Alternatively, for a patient with an upper ureteral obstruction, the upper (kidney) portion of the tubular body 130 may be uniform in diameter, tapering just in the lower (bladder) portion.

Tubular body 130 defines a central lumen or passageway 260, extending from kidney end region 140 to bladder end region 120. The inner diameter of lumen 260 is sufficient to permit passage over a guidewire. Tubular body 130 may also have openings 125 extending through its walls 250 to facilitate the flow of urine from the kidney into central lumen 260 and openings 127 to facilitate flow out of central lumen 260.

In FIG. 3, the outer diameter of elongated tubular body 130 tapers near bladder end region 120. The outer diameter of bladder end region 120 may be made as small as possible while maintaining the ability to pass over a guidewire. Elongated tubular body 130 may (but need not be) substantially straight in bladder end region 120, i.e. it does not coil or curve in the absence of external force. When tail 110 is a single filament, it typically is thinner than even the smallest portion of bladder end region 120 of the tubular stent segment. Alternatively, it may be desirable to design the tail from multiple filaments, each of which, by itself, is much thinner than the bladder end region of the tubular stent segment. Together, such a multi-filament tail has a larger effective diameter, providing additional bulk while maintaining comfort. Tail 110 may be attached at or near the end of region 120, and it extends from that attachment into the bladder. Tail 110 can be either solid or hollow. It can be generally cylindrical in shape; alternatively, it can be fluted, concave (quarter-moon)-shaped or it may assume other shapes.

The tail can have an outer diameter that is significantly less than the inner diameter of the ureter (typically 2-5 mm) and no greater than the outer diameter of the tubular segment from which it extends. For example, the tail diameter can be less than 10 F and as low as a suture (about 0.5 F). Preferably the tail diameter is between 2 F and 4 F. The length of tail 110 is preferably between 1 and 100 cm. In one embodiment, the tail is long enough so that at least a portion of it will remain in the bladder, and effectively the entire tail cannot migrate up into the ureter. A length of between 1 and 40 cm can be effective for this purpose. Tail 110 is flexible and, upon application of force, can be curved, but also has memory such that when the force is removed, it is generally straight.

Stent 100, including tail 110 and tube 130, may be a single unit. Thus, tail 110 can be a unified piece, extending from bladder end region 120 with no additional attachment means. Alternatively tail 110 can be secured to elongated tube 130 or bladder end region 120 by physical or mechanical methods.

Figure 4B:
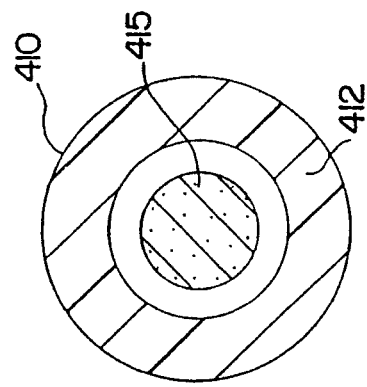
FIG. 4B is a section taken along 4B-4B of FIG. 4A.

As shown in FIG. 4A, a suture 415 can be inserted through an opening 418 in the tubular member and then threaded through the lumen 417 of tubular member 430. In FIG. 4B, tail 410 is a hollow member having suture 415 threaded through its inner lumen 412.

Figures 5A, 5B:
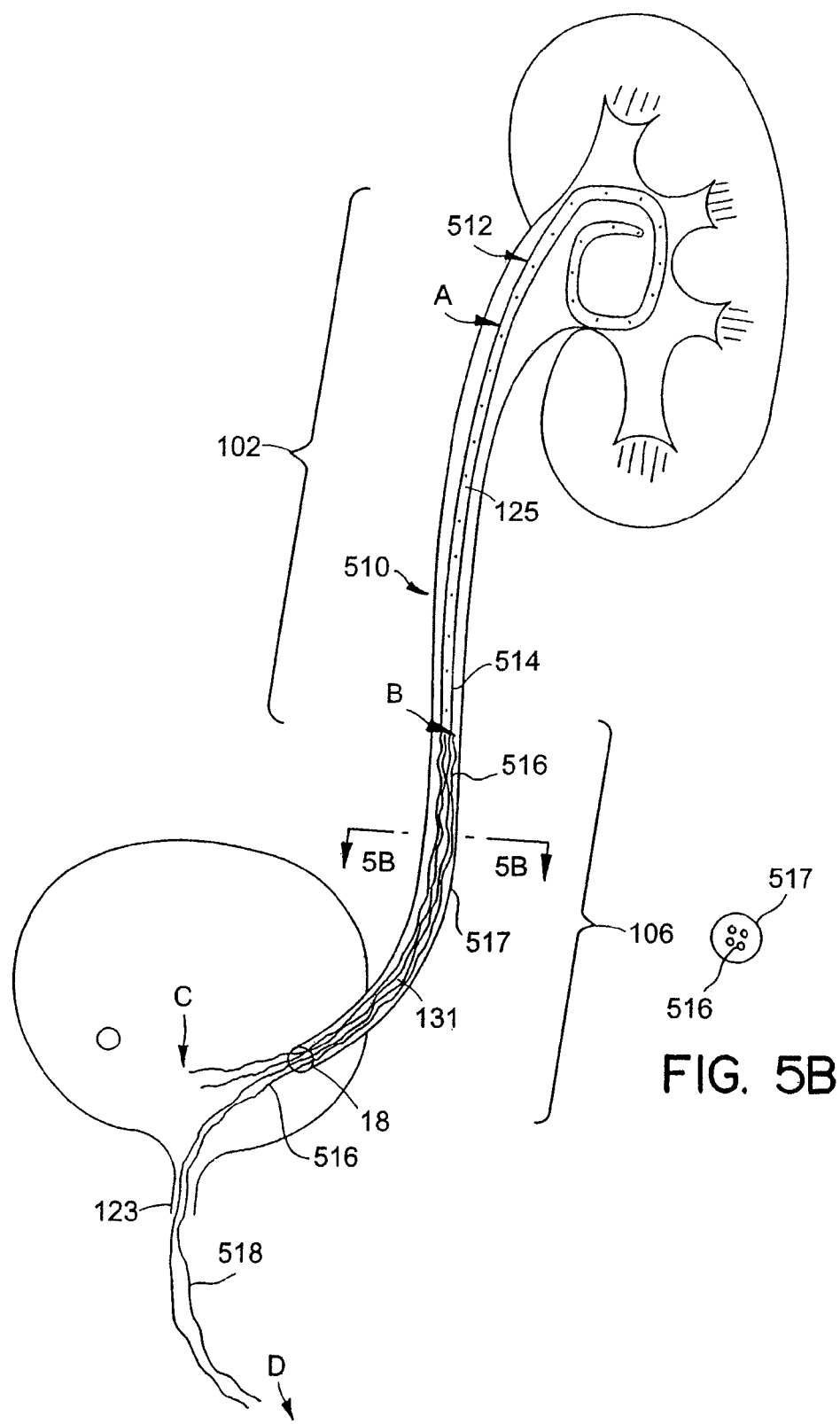
FIGS. 5A and 5B are schematic representations of another stent according to the invention, depicted in place.

FIG. 5 is a schematic of another stent 510. The kidney end A of the stent has a pre-formed memory bend, to coil 512 as shown. Kidney end A is larger and more rectangular to help prevent upward as well as downward stent migration. End A may be closed or tapered to accommodate various insertion techniques. For the upper portion (A-B) of the stent, diameter, lumen size, perforations and materials are conventional. The lower end 514 of the tubular stent segment ends at B. The distance A-B could vary depending on the patient's anatomy. At B, the stent is tapered (or at least smooth and constant in diameter).

Two or more monofilament or coated (plastic or silicone) threads 516 exit from the lumen or from the stent wall. These threads only partially fill the ureter and are as flexible (soft) as possible. Typically, they are cut to a length that forces confinement within the bladder.

The portion of the upper segment 512 lying within the renal pelvis (e.g., from the kidney end of the stent to point A) is expanded so that it is larger in section, and it may even be oval or rectangular in cross-section, to help prevent upward as well as downward stent migration. The kidney end of the stent may be closed and/or tapered to accommodate the desired insertion technique. The upper portion 512 is made of a relatively stiff material (among the materials currently used in ureteral stents), and it should be designed to effectively restrict the motion of the stent to prevent proximal as well as distal migration of the catheter during normal physiological activity (required because the lower pre-formed portion is deleted). The length of the straight portion of the upper segment (FIG. 5A point A to B) will vary with patient size and anatomy. In the preferred configuration, the upper segment extends more than halfway down the ureter when in proper position. The lowest end of the upper segment (FIG. 5A point B) should be tapered or beveled to facilitate withdrawal. Otherwise, the upper segment is a typical stent in diameter, materials, and shape.

The lower segment (FIG. 5A point B to point C) consists of two or more (e.g., four) monofilament, plastic coated or silicone coated threads (shown in section in FIG. 5B) which extend from the lumen or sidewall of the lower end of the upper segment (FIG. 5A point B) along ureter 513 into the bladder. These threads are extremely flexible, and their diameter is selected to maintain a passage for urine flow and yet drastically reduce bladder and ureteral irritation. By avoiding distortion of the ureter wall, the threads may inhibit urinary reflux as well. The threads should be long enough to reach well into the bladder (FIG. 5A point C), but not so long as to wash into the urethra with voiding. One thread 518 (or two or more threads in a loop) may be long enough to exit through the urethra (FIG. 5A point B to point D) to permit ready removal by pulling (avoiding cystoendoscopy).

These extended threads may also be used for stent exchange, in which a second catheter is exchanged for the catheter already in place. According to that procedure, these extended threads are captured with a snare that has been inserted through the central lumen of a second catheter. The snare is used to pull the threads through the lumen as the second catheter is advanced into the ureter. A guidewire is then inserted through the central lumen of the second catheter to the kidney (outside the first catheter's tubular body). The first stent can then be removed by pulling on the threads, leaving the guidewire in position for placement of a new stent using standard techniques.

Figure 6A:
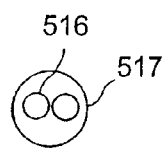
FIGS. 6A-6D depict alternative cross-sections of the tail of a stent according to FIG. 5.
Figure 6B:
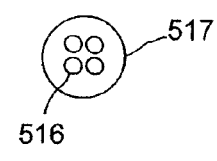
Figure 6C:
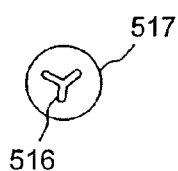
Figure 6D:
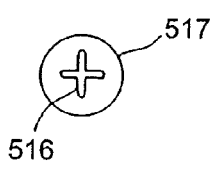

FIGS. 6A-6D are alternative cross sectional sketches (taken at the same location as FIG. 5B) of some possible arrays of threads passing within the lower ureter 517. Multiple threads 516 (2 and 4, respectively) are shown in FIGS. 6A and 6B. A substantially similar conduit could be achieved by fluted type cross sections in a single filament FIGS. 6C and 6D). The shapes of FIGS. 6C and 6D could also be effective in reducing stiffness and hence irritability at the bladder end (I.e., lower segment), e.g., in a single filament design. Multiple threads may have the advantage of better surgical manipulability and superior comfort to the patient.

Figure 7A:
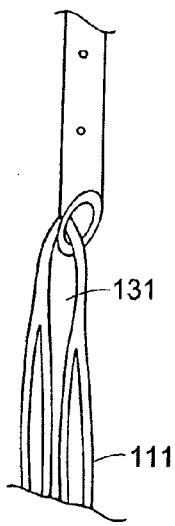
FIG. 7A is an enlargement of a portion of FIG. 7.
Figure 7:
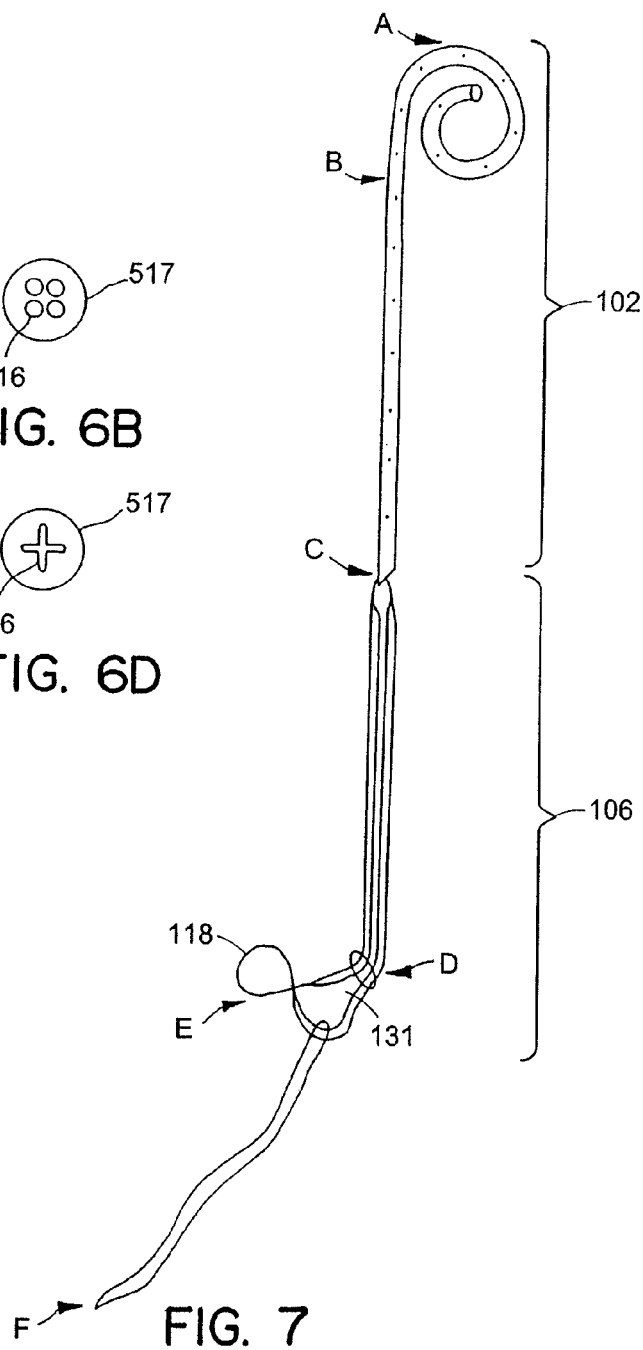
FIG. 7 is a schematic representation of yet another stent according to the invention, having an extraction thread.
Figure 8:
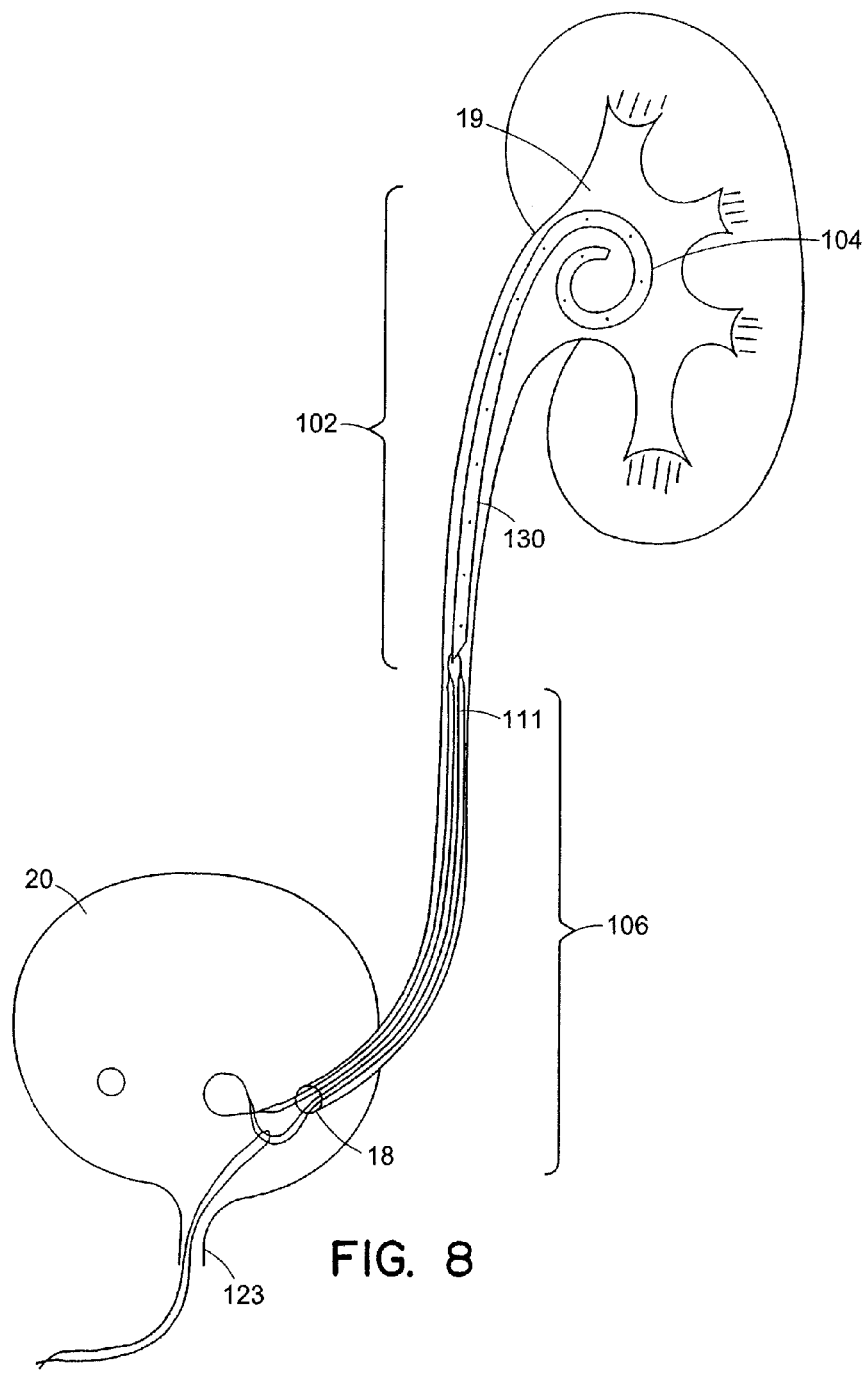
FIG. 8 is a schematic representation of the stent of FIG. 7 shown in position.

Further refinements are described below and in FIGS. 7 and 7A which deal with: a) proximal or upward stent migration of either the entire stent or individual threads in the lower segment independent of upper segment movement; b) bunching of one or more threads within the ureter so as to obstruct flow or cause ureteral injury or knotting at the time of removal; and c) in multi-thread embodiments, discomfort and/or reduced drainage through the ureter resulting from the use of threads of different lengths. In FIG. 7, a 6 F stent is depicted, which is generally a good size for adult urinary systems. It is large enough to provide good drainage and small enough to minimize local irritation and inflammation of the ureter. In this embodiment, the upper segment need be only a single loop of conventional size because a change in the design of the lower segment (see later discussion and FIG. 8) should prevent proximal migration. The upper segment (FIG. 7 point A to point C) is constructed of a relatively firm material because, during insertion, the pusher tubing should be removed after the guidewire is removed. This means that there will be some drag on the threads during removal of the pusher tubing which could dislodge the stent if the coil (FIG. 7 point A to point B, about 2.5 cm) does not provide adequate resistance. The coil may be tapered or closed depending on the insertion technique desired (i.e., over a previously placed guidewire).

FIG. 7 point B to point C can have an approximate length of 12 cm. This is long enough to prevent dislocation of the upper segment in a large renal pelvis and short enough to end well above the point where the ureter crosses the common iliac vessels. At the iliac vessels, the ureter takes a fairly sharp turn and the threads will more easily follow the natural curves at this point. This design should reduce the inflammation that is normally seen in this region when a conventional double-1 stent is left indwelling on a chronic basis.

Figure 8A:
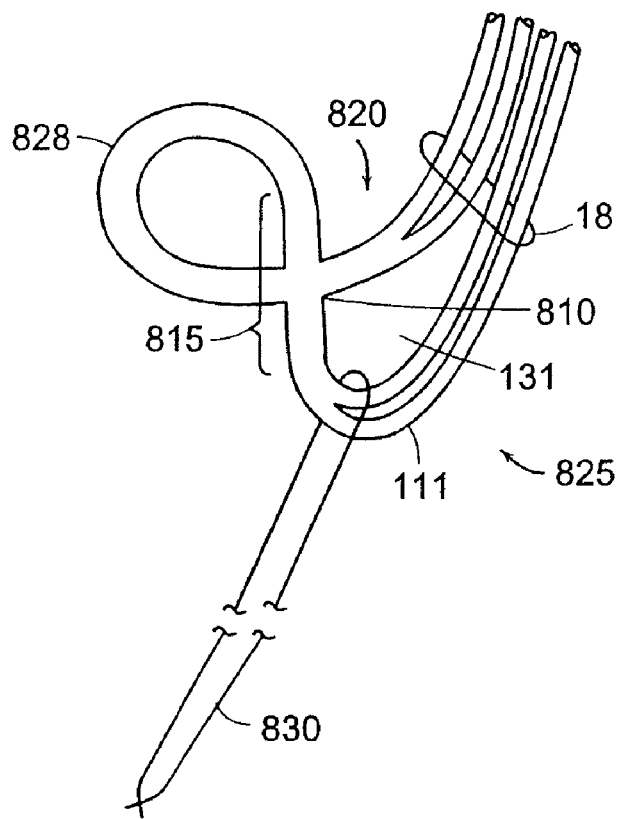
FIG. 8A is a detail of the connection between the tail and the extraction thread.
Figure 8B:
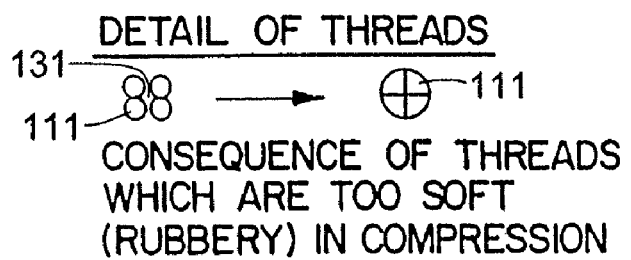
FIG. 8B is a cross-section of threads of differing softness, showing the effect of compression on interstitial space.

The junction of the upper and lower segments at FIG. 7 point C is important. See FIG. 7A, which enlarges this junction. At point C (FIG. 7) the threads are attached to the upper segment in a manner that achieves the following goals: 1) the threads are securely attached to the upper segment and to each other (at least for a short distance of about 0.8 mm) so that their orientation to themselves is maintained (to the maintenance of lower end asymmetry); 2) the threads do not obstruct the lumen of the upper segment and they allow for the easy passage of a standard guidewire (e.g., 0.035 guidewire); 3) the transition diameters in this region closely preserve the 6 F standard so that this point can pass in both directions smoothly throughout the instruments used for insertion and through the ureter; 4) there is no cause for a localized ureteral obstruction; and 5) there is an effective abutment for the pusher tubing. For an average size ureter a good starting string diameter for a four string lower segment (FIG. 7 point C to point E) would be 0.020 inches. A simple monofilament nylon thread is an easy potential solution but may be too stiff. A more supple monofilament or woven thread with silicone or other coating may be required to achieve minimal irritability. However, the threads can be sufficiently resistant to compression so that tissue-generated pressures cannot collapse the interspaces of the threads. See FIG. 8B, showing cross-sections of threads (left) which retain interstitial space under some modest compression, and of threads (right) which are so soft that they compress into a plug with reduced interstitial space. These threads may have centimeter markings beginning at a point no more than 20 centimeters from point B (FIG. 7) so that functional ureteral and total stent length may be noted.

The portion of the lower segment that lies within the bladder when the stent is in proper anatomic position (FIG. 7 point D to point E) is important to both comfort and function. Proximal migration can be controlled by using asymmetrical lengths of the thread pairs, with one pair being 2 cm longer that the other pair, so that the fused junction 810 of these threads tends to intersect with the ureteral orifice 18 at an angle (e.g., ~90°) with the stiffened area 815 having a length of 6 mm (see detail FIG. 8A). In the ideally fitted stent of this embodiment, the thread pairs will extend beyond the ureteral orifice (FIG. 7 point D) by 1 cm at the short limb 820 and 3 cm at the long limb 825. However, this lower segment configuration allows for considerable tolerance in sizing (unlike unsecured independent threads which must be selected to have a length so as to avoid upward migration of the thread through the ureteral orifice 18) and a chosen length which is 1 cm shorter or 2-3 cm longer than the ideal length should be satisfactory. Using this configuration the threads should form a continuous loop 828 of 3.5 cm length to prevent free ends from poking the bladder wall or prolapsing through the urethra. Buoyant threads may add to patient comfort, because they will float away from the trigone region of the bladder, where most of the sensory nerve fibers are located. A typical small gauge filament extraction thread 830 may be attached to the longer limb 825 of the thread pairs, which is a suitable pulling point for removal.

From this embodiment, a small diameter pusher tubing of 4-4.5 F should be used to aid insertion. Soft Percuflex® material can be used for the lower segment and firm or regular Percuflex® can be used for the upper segment.

The bladder end should be easily inserted using instruments, and it should prevent proximal migration of the stent. The design of FIG. 7 will avoid tangling and migration of the stent. Alternatively, soft Percuflex® material, for example, has good resistance to extreme flexion at small radii (e.g., even 0.020" diameter) so that a simple continuous loop extending from the junction of the upper and lower segments (see FIG. 9) may be adequate to prevent upward migration. The design of FIG. 9 also has the advantage of relative ease of manufacture and relative ease of insertion, as well as ease and comfort of removal.

Other dimensions that can be used (without limitation) are 12 cm straight portion of the upper hollow shaft, and 12 cm, 14 cm, or 16 cm length of added loops of soft Percuflex@ material. For material with a 0.020" diameter, either 2 or 3 loops may be used, providing 4 or 6 strings, total. For 0.040" inch material, either 1 or 2 loops is recommended.

Figure 9:
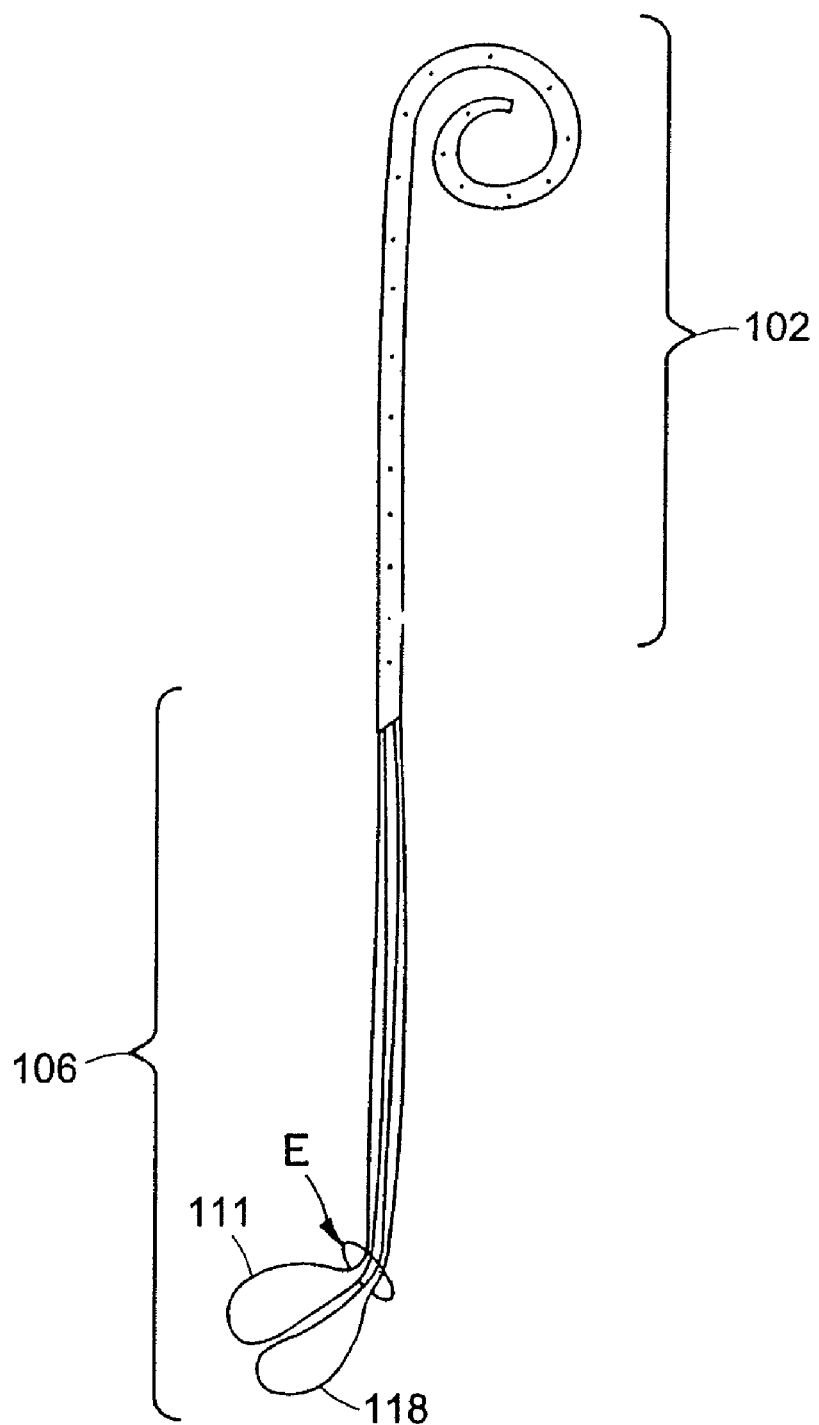
FIG. 9 shows an alternative embodiment of the stent.
Figure 10:
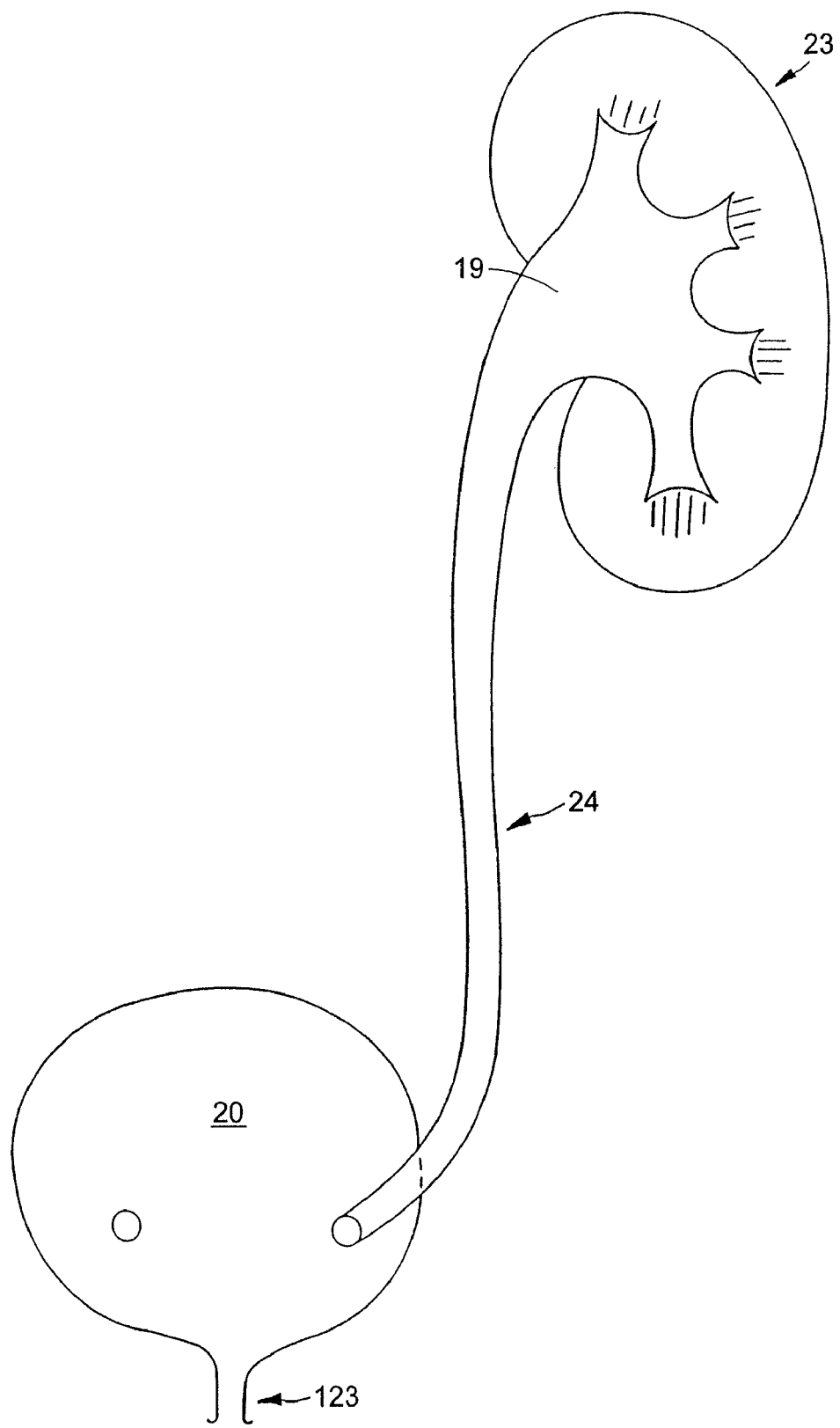
FIG. 10 is a schematic drawing of the human urinary tract without a stent, showing the renal pelvis, the kidney, the ureter, and the ureteral orifices opening into the bladder.
Figure 11:
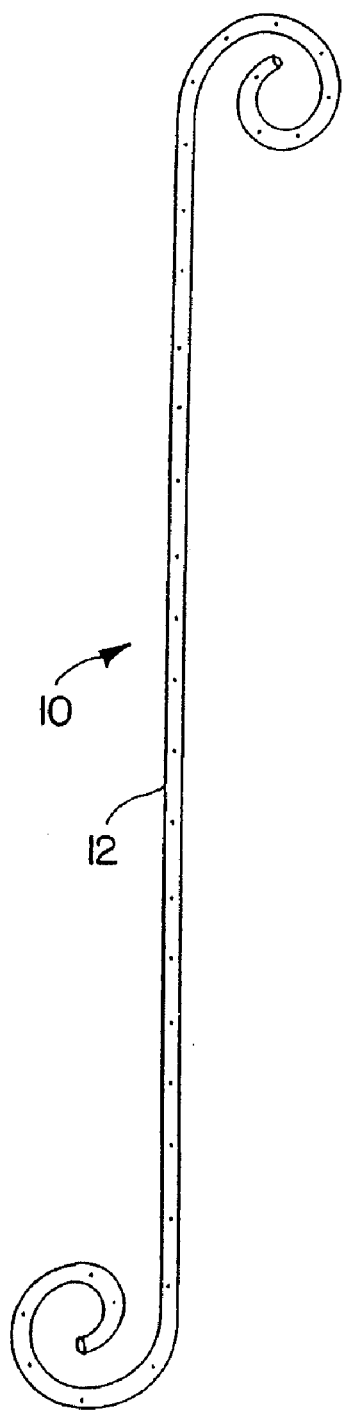
FIG. 11 depicts a prior art double-J stent outside the body.
Figure 12:
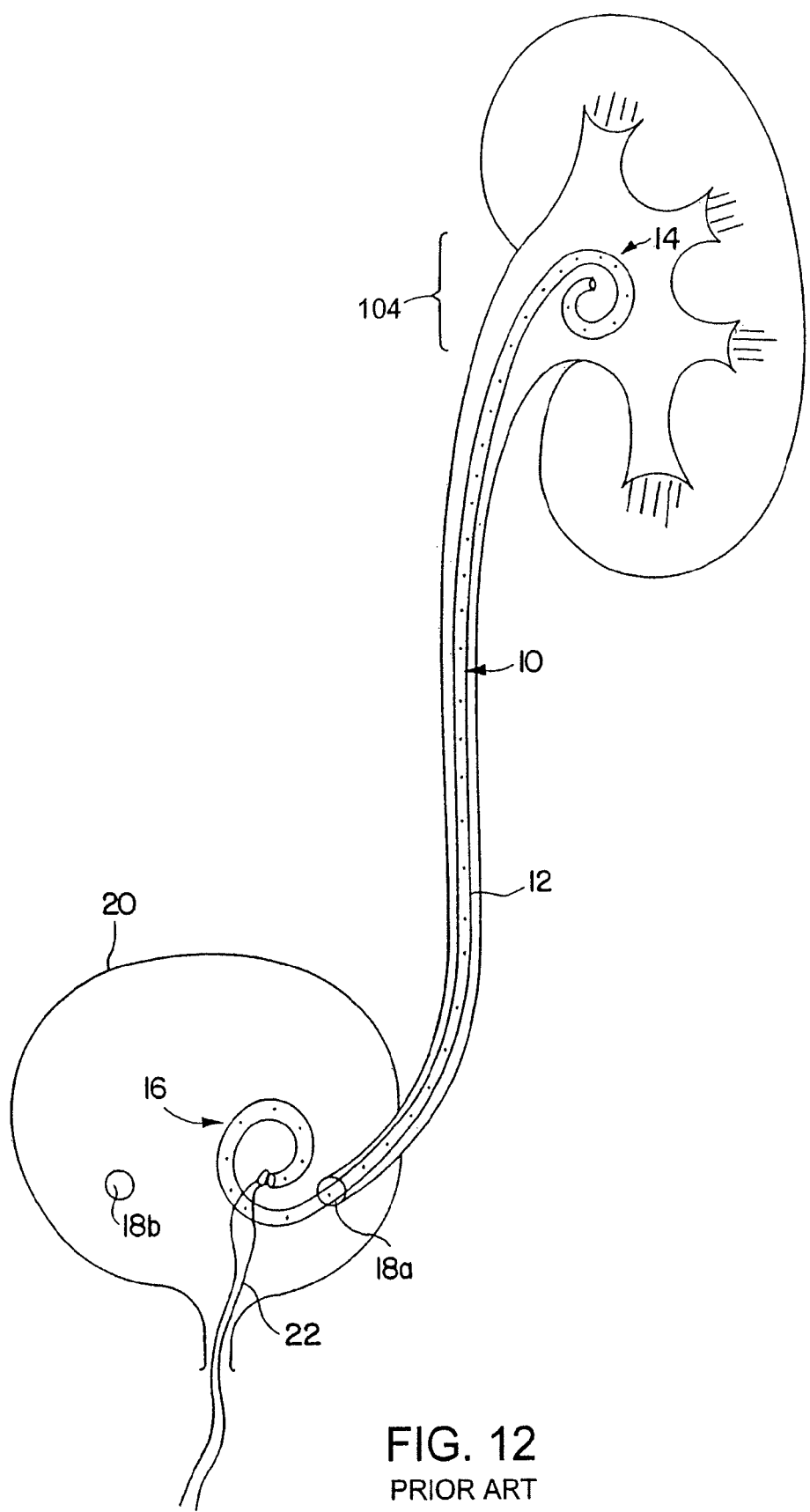
FIG. 12 depicts a prior art J indwelling ureteral stent in position.

FIG. 9 shows such an alternative embodiment having a simple coil at the kidney end. The lower end is constructed of looped stringlike elements with ends fused at the junction between the lower and the upper end. Therefore, there are even numbers of string elements, with no free ends. Circle E in FIG. 9 represents an idealized depiction of the ureteral opening into the bladder. While not shown in FIG. 9, the loops may be fused over a very short distance at the bladder end in order to prevent tangling of loops and to improve stent handling. Any conventional means of fusion may be used. Optionally, organization of the loops can be maintained by pre-placing them inside the pusher tubing using a long monofilament nylon loop tail, similar to those used for the non-invasive removal stents (i.e. without sensor endoscopy).

Methods for insertion and removal of ureteral stents are known in the art. Generally, stent placement is achieved by advancing the tubular stent segment over a guidewire in the ureter. A pushing catheter passes the tubular segment into the kidney, while maintaining the tail in the bladder. Other methods such as a stiff sheath can be used to position the stent. Once in position, the sheath can be removed.

Another embodiment of the invention features a proximal region 106 comprising threads or filaments 111 as illustrated in FIG. 13. The fine flexible filaments 111 can be connected proximally to form a loop 118, or the loop can be formed from a continuous filament. The filaments have a small diameter, e.g., 3 French or less (i.e., less than, about 0.040 inches in diameter). In one configuration individual filaments preferably have no internal lumen. The illustrated embodiment includes a distal region 102 that includes a tubular body 130 having openings 125 and defining a lumen 260 therein. The proximal region 106 can be integrally formed with distal region 102. A distal portion of the distal region 102 includes a distal retention structure 104, configured to maintain placement of the distal end of the stent within a renal pelvis 19. As illustrated in FIG. 13A, an interstitial space 131 is defined between the filaments. The interstitial space 131 is in fluid communication with lumen 260 of the tubular body 130. The interstitial space provides for drainage, e.g., of urine, from the kidney (e.g., the renal pelvis 19) through the lumen 260 of the tubular body 130 and into the bladder 20 of a patient's body. Such drainage can occur in the space between the filaments 111 and/or along surfaces of the filaments.

Figure 14:
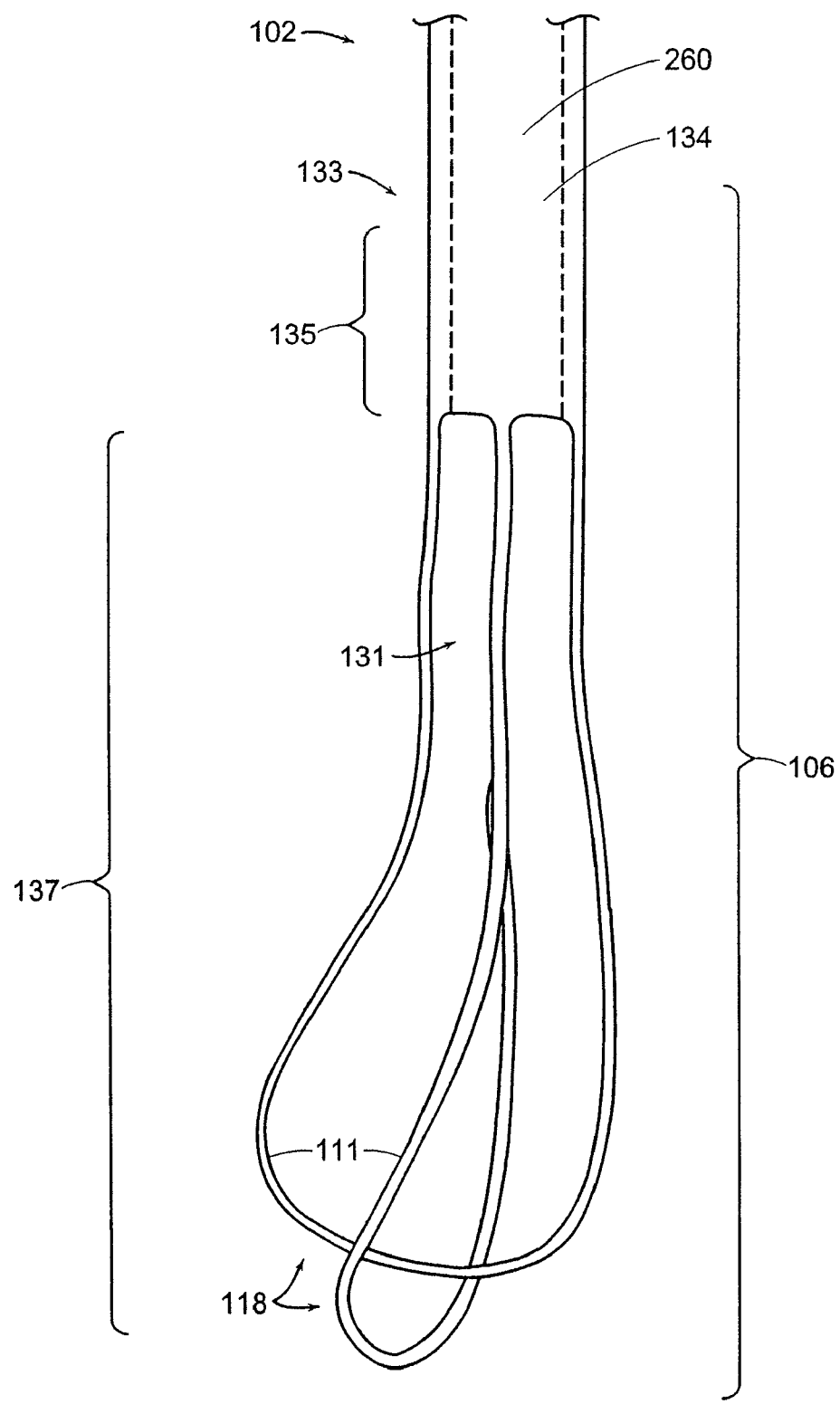
FIGS. 14 and 14A depict an embodiment of a ureteral stent including a pliable portion.

FIG. 14 depicts an embodiment of a ureteral stent having a proximal region 106 that includes a plurality of loops. The proximal portion 137 of the proximal region 106 includes loops 118 fanned from one continuous filament, or, alternatively, the loops 118 can be formed from at least a portion of a plurality of filaments 111. In the illustrated embodiment, the proximal region includes two loops 118 formed from two continuous filaments 111. In an alternative embodiment, the proximal region includes two loops 118 formed from a portion of four filaments. Each loop is formed of at least two filaments, preferably by joining the proximal ends of two filaments together. A pliable portion 135 is disposed adjacent to the proximal portion 137, and can comprise a soft portion of tube compressible by pressure (e.g., body pressure). The filaments 111 are configured to minimize any sharp exterior edges at the interface between the filaments and the pliable portion 135. In some embodiments, the lumen 260 of the tubular body 130 extends through to the pliable portion 135, as illustrated. The proximal region 106 also includes a distal portion 133 comprising a junction 134 between the pliable portion 135 and the distal region 102. The pliable portion can be a distinct section of tube incorporated into the stent, or the pliable portion can be a section of the stent that is integral with the distal region. Preferably, the pliable portion is softer than distal portions of the stent along the distal region.

The filaments 111 of the proximal portion 137 define an interstitial space 131. Interstitial space 131 is in fluid communication with lumen 260, and provides for flow between the kidney and the bladder 20.

Figure 14A:
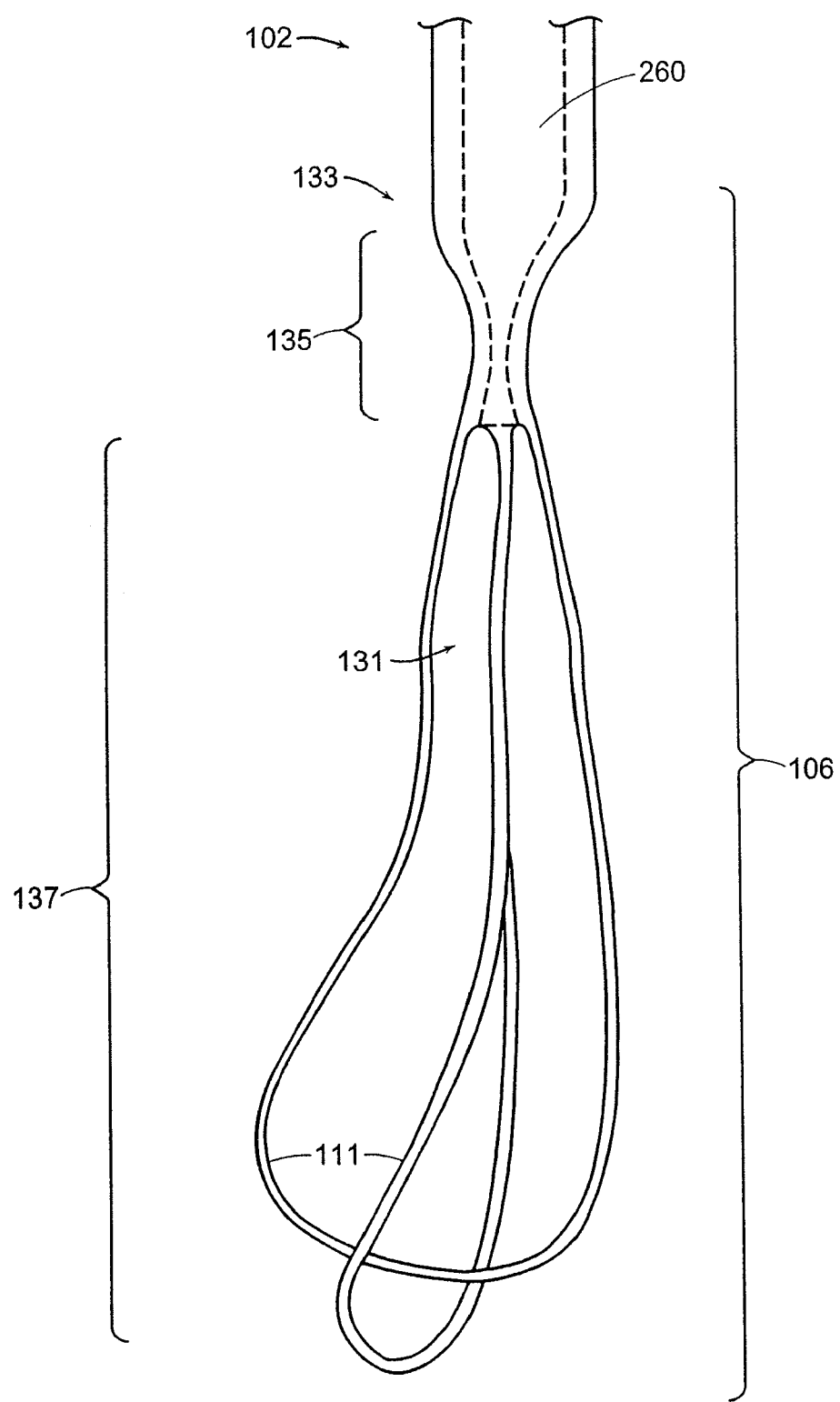

As illustrated in FIG. 14A, the pliable portion 135 is compressible upon exertion of a pressure by the body, such as a pressure exerted by the ureteral orifice 18. Preferably, the stent is positioned within the body such that the pliable portion 135 is located at or near the ureteral orifice 18. In one embodiment, the pliable portion 135 extends distally into the ureter for a distance of approximately 2-3 centimeters (e.g., FIG. 16B). The pliable portion 135 of this embodiment can extend through the ureteral orifice 18 and into the bladder (e.g., FIG. 16A). In such embodiments, the overall loop length can be 3-6 centimeters with no portion of the loop residing in the proximal 2-3 cm of the ureter. This proximal portion of the ureter is believed to be highly innervated. Contact of this portion of the ureter with the softer material of the pliable portion provides increased comfort to the patient.

Constriction of the ureteral orifice by the patient can exert a pressure on the pliable portion 135 resulting in constriction of the pliable portion, thereby reducing or eliminating the flow area available in the portion of the lumen 260 disposed within the pliable portion. This reduction in flow area reduces or eliminates painful urine reflux that can be experienced by the patient. In this way, the pliable portion can collapse sufficiently to inhibit urine reflux. When the body pressure is removed, the pliable portion reopens.

In one embodiment, the overall length of the loops 118 in FIGS. 14 and 14A can be about 4-6 centimeters. For example, a loop with a length of 5 centimeters can be formed from a single filament 111 having a length of about 10 centimeters, or from two filaments 111 each having a length of about 5 centimeters. The loop 118 is designed to be sufficiently long to remain in the bladder 20 when the distal retention structure 104 is positioned within the kidney. At the same time, the length of the filaments should be short enough to substantially reduce contact of the loop with the urethra 123. As stated previously, contact with the urethral opening can cause patient discomfort. Although incidental contact can generally be tolerated by a patient, extensive contact of a loop or filament across the bladder neck or into the urethra can cause extreme discomfort. This contact can also result in obstruction of the flow of urine from the bladder through the prostatic urethra during voiding. Moreover, routine movement of the kidney and the bladder can result in corresponding relative motion along the stent length of about 2 centimeters. Proper sizing of the length of the filament loops provides effective compensation for this movement. The length of the loop can be established to maintain at least a portion of the loop within the bladder after intubation, including upon routine movement of the kidney and the bladder. By way of example, a loop length of approximately 5 centimeters can be effective for this purpose.

Contact of any portion of the proximal region 106 with the trigone can cause patient discomfort. Such contact should be minimized or eliminated. Embodiments of the invention accomplish this by providing no significant retention force for the stent within the bladder 20. That is, the filaments have a retention force insufficient to maintain the stent within the bladder. The flexible filaments are designed to free float within the bladder, making little or no contact with the trigone. Such contact is also minimized by having no stiffened or rigid areas within or about the filaments, and by minimizing their diameter, volume, surface area, and mass. Although the distal region of the stent can have a hardness of about 110 Shore A, the proximal region is generally much softer, having a Durometer hardness of approximately 60-80 Shore A. In some embodiments the hardness of the stent is gradually decreased from a distal location, e.g., 141, of the distal region to a proximal location, e.g., 142, of the proximal region. Preferably, the proximal region is integrally formed with the distal region in such embodiments.

The lower hardness limit (i.e., the softness limit) of the filaments can be determined by the tensile strength required to withdraw the stent from the body. More specifically, extubation of the stent from the body can be achieved by grasping the filaments and pulling the stent out of the body via the urethra. This is most efficiently achieved in embodiments having filaments that are formed into loops, since an instrument can more readily grasp a loop than a single filament. The tensile strength of the filaments should be sufficient to prevent breakage of the filaments as the stent is being withdrawn from the body. If extubation is not a concern, filaments of reduced tensile strength, and hence of smaller diameter, can be used with the invention.

Figure 15:
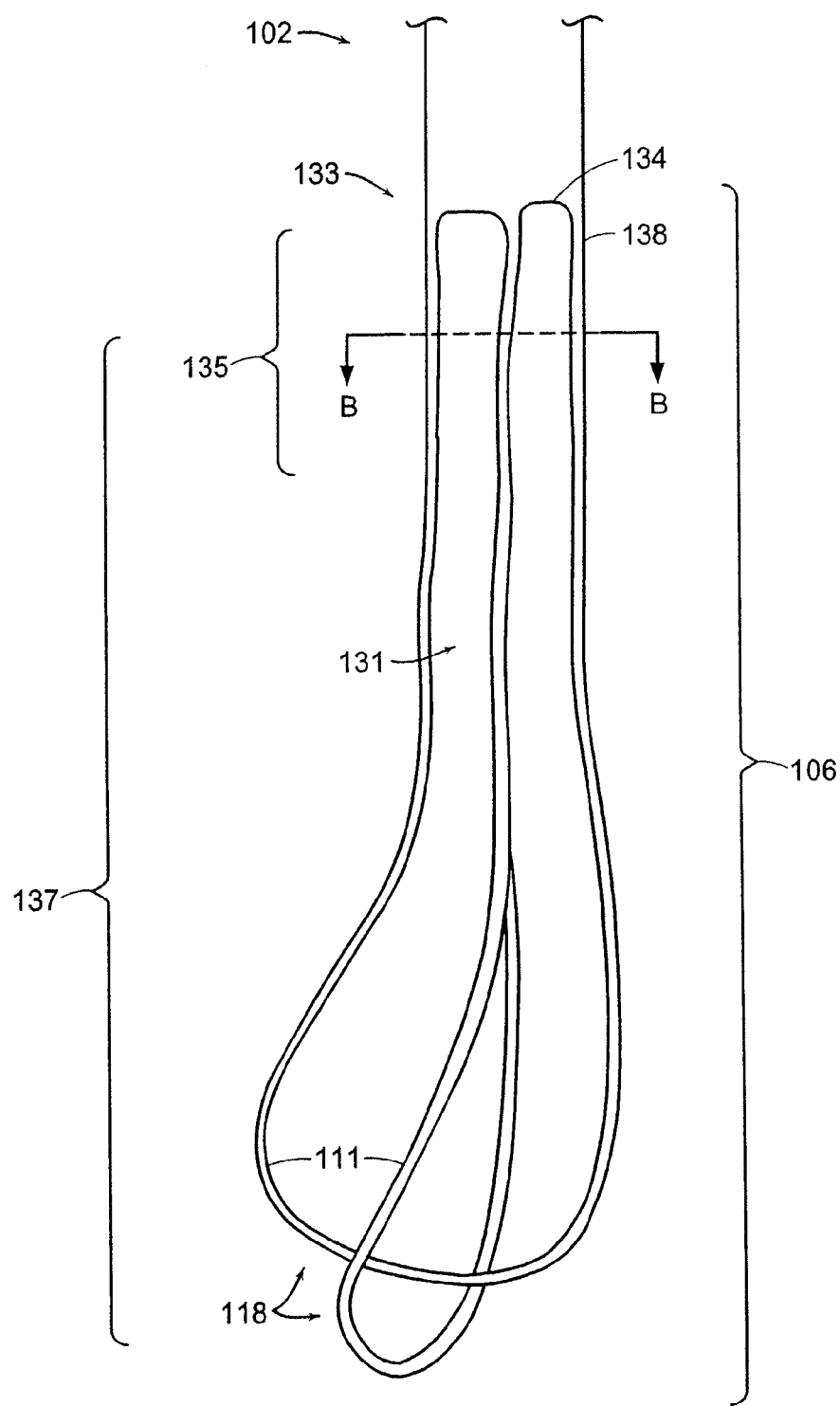
FIGS. 15, 15 A, 15B, 15C, 15C', and 15C" illustrate embodiments of ureteral stents including a pliable portion, in which the pliable portion includes loops with one or more flexible filament(s).

In some embodiments the pliable portion 135 comprises a distal end 138 of the plurality of filaments 111, as illustrated in FIG. 15. The proximal region 106 includes a plurality of loops. Specifically, the proximal region 106 includes two loops 118 each formed from one continuous filament. Alternatively, the two loops 118 can be formed from a portion of four filaments 111; each loop can be formed from two filaments by joining them filaments together. A pliable portion 135 is formed from a portion of the flexible filaments 111 and is disposed adjacent to the proximal portion 137. The filaments 111 are configured to minimize any sharp exterior edges at the interface between the filaments and the junction of the distal portion 133, thus minimizing any potential irritation to the intramural ureter. The filaments 111 of the proximal portion 137 define an interstitial space 131. The lumen 260 of the tubular body 130 continues through to the pliable portion 135, as illustrated. Thus, the interstitial space 131 is in fluid communication with lumen 260, and provides for flow between the kidney and the bladder 20.

Figure 15A:
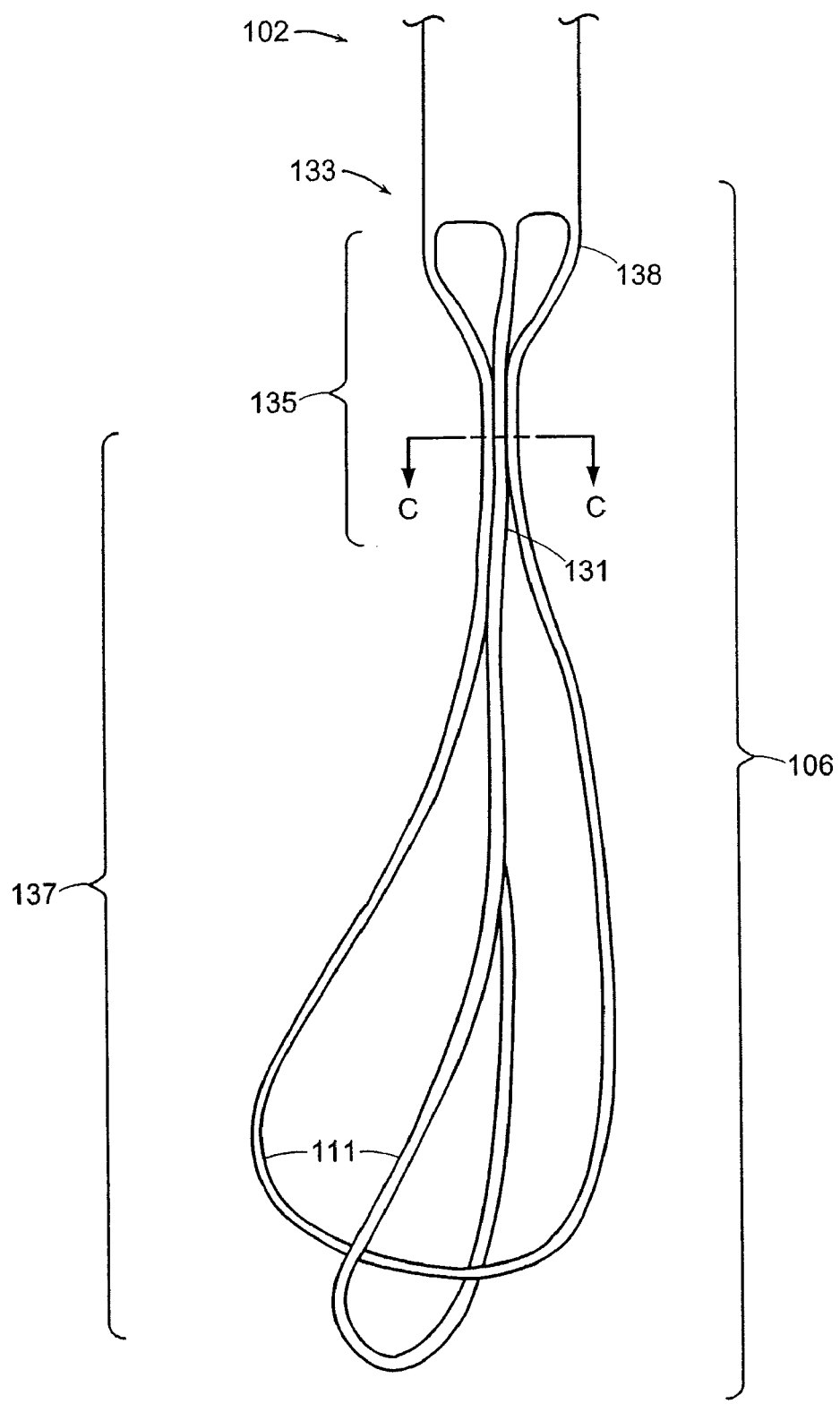

As illustrated in FIG. 15A, the filaments of the pliable portion 135 are compressible upon exertion of a pressure by the body, such as a pressure exerted by the ureteral orifice 18. In one embodiment, the stent is positioned within the body such that the filaments of the pliable portion 135 pass through the ureteral orifice 18 and extend distally into the ureter for a distance of approximately 2-3 centimeters. Because the proximal portion of the ureter is believed to be highly innervated, contact of this portion of the ureter with the softer material of the flexible filaments provides increased comfort to the patient.

Constriction of the ureteral orifice by the patient can exert a pressure on the filaments of the pliable portion 135 resulting in constriction, thereby reducing or eliminating the flow area through and about the interstitial space 131 of the proximal region 106 at the ureteral orifice 18. This reduction in flow area reduces or eliminates painful urine reflux that can be experienced by the patient upon voiding. In this way, the filaments of the pliable portion can be collapsed sufficiently to inhibit urine reflux. For example, FIG. 15B depicts a cross-sectional view taken at section B-B in FIG. 15. In this uncompressed state the flow area presented in interstitial space 131 is large. Upon constriction, e.g., by ureteral orifice 131, the flow area can be reduced as illustrated in FIG. 15C, representing a section taken at C-C of FIG. 15A. As can be seen from the figure, ureteral orifice 18 is contracted and the filaments 111 have been pressed closer to each other. In some embodiments, the filaments can be compressed to the point where some or all of them contact each other, as shown in FIGS. 15C' and 15C", further reducing or even eliminating the interstitial space 131.

The amount of interstitial space 131 remaining upon compression of the filaments can in part be determined by the physical properties of the filaments. In some embodiments, only partial compression of the interstitial space formed between the filaments 111 is achieved (e.g., FIG. 15C). In other embodiments, virtually all of the central interstitial space at a certain point along the length of the filaments can be eliminated by body pressure. In embodiments including filaments of an even softer material, flow area about the periphery of the filaments can also be eliminated or reduced (not shown). In many of these embodiments, urine flow through the ureteral orifice 18 can be virtually eliminated. It can be seen that upon the exertion of adequate force the filaments 111 not only contact each other, but if soft enough, they can be deformed by the pressure to further reduce any flow area. The ureteral stent of the invention thus allows urine flow reduction, including the reduction or elimination of urine reflux, to be achieved while minimizing irritation to the patient. When the pressure from the ureteral orifice is released, the filaments separate from each other thereby recreating the interstitial space.

In one embodiment, the overall length of the loops 118 in FIGS. 15 and 15A can be about 7-9 centimeters. Similar to the discussion above, a loop 118 with a length of 8 centimeters can be formed from a single filament 111 having a length of about 8 centimeters, or from two filaments 111 each having a length of about 8 centimeters. The loop 118 is designed to be sufficiently long to remain in the bladder 20 when the distal retention structure 104 is positioned within the kidney. In addition, the length should be sufficiently short to substantially reduce contact of the loop with the urethra 123, since contact with the urethra can cause patient discomfort. It can also result in obstruction of the flow of urine from the bladder through the prostatic urethra during voiding. Moreover, routine movement of the kidney and the bladder can result in corresponding relative motion along the stent length of about 2 centimeters. Proper sizing of the length of the filament loops can provide effective compensation for this movement. The length of the loop can be established to maintain at least a portion of the loop within the bladder after intubation, including upon routine movement of the kidney and the bladder. For this embodiment, a loop length of approximately 8 centimeters can be effective for this purpose.

Because contact of any portion of the proximal region 106 with the trigone also causes patient discomfort, such contact should be minimized or eliminated. Embodiments of the invention accomplish this by providing no significant retention force for the stent within the bladder 20. That is, the filaments 111 have a retention force insufficient to maintain the stent within the bladder. The flexible filaments are designed to free float within the bladder, making little or no contact with the trigone. Such contact is also minimized by having no stiffened or rigid areas within or about the filaments, and by minimizing their diameter, volume, surface area, and mass. Although the distal region of the stent can have a hardness of about 80-110 Shore A, the proximal region is generally much softer, having a Durometer hardness of approximately 60-80 Shore A. In some embodiments the hardness of the stent is gradually decreased from a distal location, e.g., 141, of the distal region to a proximal location, e.g., 142, of the proximal region. Preferably, the proximal region is integrally formed with the distal region in such embodiments.

The lower hardness limit (i.e., the softness limit) of the filaments 111 can be determined by the tensile strength required to withdraw the stent from the body. More specifically, extubation of the stent from the body can be achieved by grasping the filaments and pulling the stent out of the body via the urethra. This is most efficiently achieved in embodiments having filaments that are formed into loops, since an instrument can more readily grasp a loop than a single filament. The tensile strength of the filaments should be sufficient to prevent breakage of the filaments as the stent is being withdrawn from the body. If extubation is not a concern, filaments of reduced tensile strength, and hence of smaller diameter, can be used with the invention. Patient discomfort can thus be further reduced.

Figure 16A:
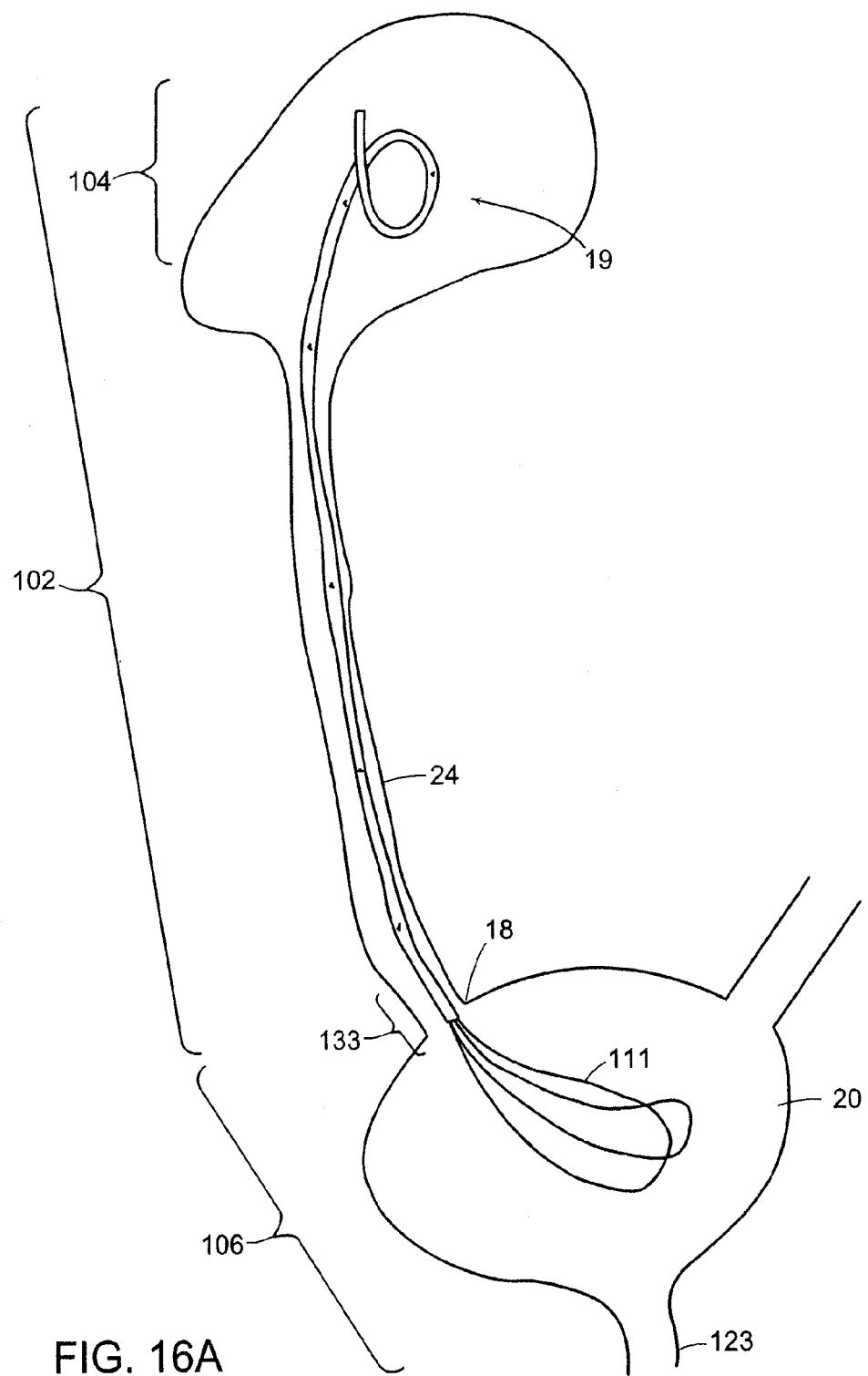
FIGS. 16A-16B illustrate general placement in the body of embodiments of ureteral stents comprising loops formed of one or more flexible filament(s).

FIG. 16A illustrates placement of an embodiment of the invention within the body of a patient, in which the stent comprises two loops with a length of approximately 5 centimeters and a pliable portion including a soft portion or segment of tube compressible by body pressure. The distal retention structure 104 of the distal region 102 is located in the renal pelvis 19. The portion of the pliable portion 135 comprising the soft tube is encompassed by the ureteral orifice 18, and filaments of the proximal portion are disposed within the bladder 20. Loops 118 freely float within the bladder and have a length sufficient to maintain at least a portion of the filaments 111 within the bladder, including upon routine movement of the kidney and the bladder. The length of loops 118 is insufficient to contact the opening of the urethra 123.

Figure 16B:
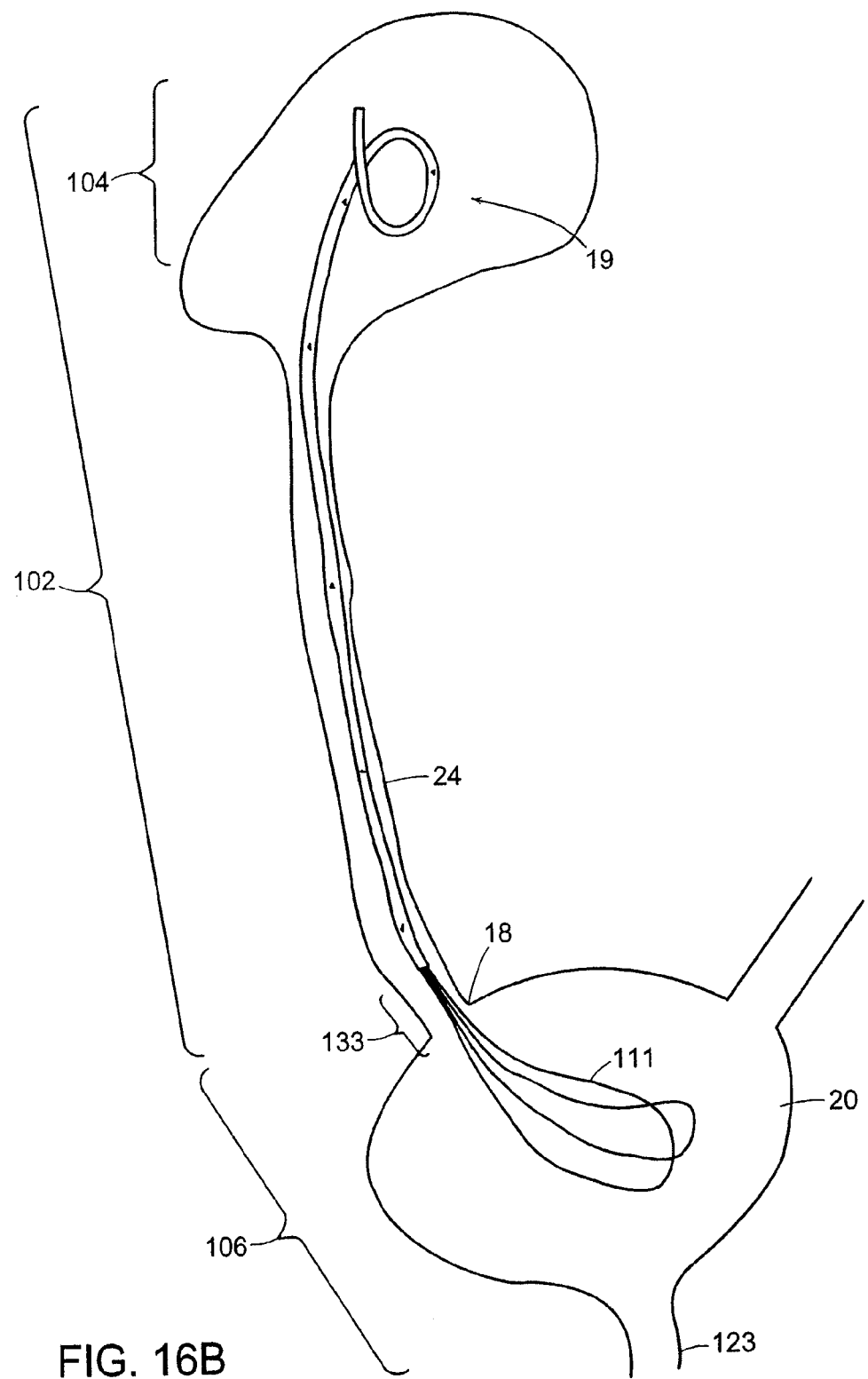

FIG. 16B illustrates placement of an embodiment of the invention. The stent includes two loops (having a length, for example, of 8 centimeters) and a pliable portion including a portion of the flexible filaments compressible by body pressure. The distal retention structure 104 of the distal region 102 is located in the renal pelvis 19. The portion of the pliable portion 135 comprising the distal ends 138 of the flexible filaments 111 is encompassed by the ureteral orifice 18. Loops 118 freely float within the bladder and have a length sufficient to maintain at least a portion of the filaments 111 within the bladder, including upon routine movement of the kidney and the bladder. The length of loops 118 is insufficient to cross the bladder neck of the prostatic urethra 123.

Various fabrication and construction techniques can be used to manufacture embodiments of the ureteral stents of the invention. Construction of the stent 100 can include bonding a component that includes the proximal region 106, the distal region 102, and/or the filaments 111. The filaments 111 of the proximal region can be joined with the pliable portion 135 or with the distal region 102 via the junction 134 at the distal portion 133 (e.g., FIGS. 14 and 15).

Bonding of these components can be performed using heat-bonding techniques, such as by RF processes known in the art. Heat bonding functions by partially melting the plastic of a structure, allowing the melted plastic to adhere to a contacting surface or component, and allowing the plastic to cool and harden and thus form a bond. Heat bonding methods that include radio frequency bonding, induction heating and conduction heating may be used. The plastic of a first component may be selected to melt at a similar temperature as a second component so that both components are melted during the heat bonding process. Alternatively, either the first or second component may be constructed from plastic with a lower melting temperature than the other component in order that only the component with the lower melting temperature may melt during the bonding process. These techniques can also be used to form loops 118 by joining the proximal ends of two filaments 111. In embodiments comprising loops formed of one continuous filament, these techniques can be used to join the filaments with the pliable portion, the distal portion, the junction, or the tubular body.

Alternatively, the components may be bonded by the use of a bonding solvent, such as cyclohexanone and methylethylketone, for example. The bonding solvent acts by dissolving and swelling the plastic of the components. As the plastic of the components dissolve and swell, the components adhere to each other. The solvent is then removed allowing for the dissolved and swollen plastic to harden and thus complete the bonding process. These techniques can also be used to form loops 118 by joining the proximal ends of two filaments 111.

Embodiments can be fabricated from many different materials. Polymers and copolymers can be used and formed during the fabrication process, from materials such as polyurethane, polyamides, various thermoplastic elastomers, silicone, and various ethylene copolymers and block copolymers (e.g., ethyl vinyl acetate (EVA)). Other materials include biocompatible plastics, e.g., polyester, nylon based biocompatible polymers, polytetrafluoroethylene polymers, silicone polymers, polyurethane polymers, polyethylene polymers, and thermoplastic polymers. Combinations of these materials can be extruded or co extruded during the fabrication process. Portions of the stent can be made of materials with different Durometer hardness values, or the stent can be made such that the Durometer hardness value increases or decreases gradually from one location along the stent to another. In other embodiments, the entire stent can be formed of a very soft material such that the entire stent is formed from a material having a hardness of, for example, 60 Shore A.

The tubular portion of the stent may be manufactured by extruding a tube according to known techniques. The elongated tail (e.g., FIGS. 1-4) may be separately manufactured by conventional techniques and attached to the tubular portion, e.g., using biocompatible adhesive materials or heat. Alternatively, the stent may be made by injection molding the tube and the tail as a single piece, using a pin to create hollow segments. The stent may be manufactured from any of a number of biocompatible polymers commonly used inside the body, including polyurethane and polyethylene. In still other embodiments, the entire stent may be solid, so that urine is conveyed entirely on an external stent surface.

Another fabrication method, especially useful for embodiments such as those illustrated in FIGS. 13-16, includes forming, for example, four or twelve strands material into a tube. The strands can then be separated at the proximal end of the tube to form free-floating filaments for the proximal region. Loops can be formed from filaments by joining the proximal ends of two filaments with each other (although some embodiments include loops formed from one continuous filament). The joining can be performed using thermal and/or adhesive techniques. For example, the filaments can be joined with each other by positioning the materials in a mold and heating them together. These techniques can be used to join filament ends together, and to join filaments with the tube.

When fabrication techniques are used to join filaments to the tube, a mandrel can be inserted into the luminal portion of the device to maintain the luminal and/or interstitial space during heating. For example, a shaft size of 6 French can be used. A mold used with such a shaft should have a diameter that is 0.003-0.004 inches larger than the shaft diameter, to allow for insertion of the shaft, and to provide for molding of the filaments to the tube. The distal retention structure 104 can conveniently be formed from the tube.

In some embodiments the stent can be coated with a lubricious hydrophilic coating. Such a coating can be applied to the tubular body and/or the proximal region, to reduce the irritation levels attained through contact with the surrounding tissue/mucosa in the bladder. Care should be taken to ensure compatibility of the coating with any polymeric materials used.

Methods such as these can be used to produce embodiments with consistent and smooth exterior surfaces and outer diameters, for example, with diameters of 4-10 French.

Having thus described certain embodiments of the present invention, various alterations, modifications, and improvements will be apparent to those of ordinary skill. Such alterations, modifications, and improvements are intended to be within the spirit and scope of the invention. Accordingly, the foregoing description of embodiments of the invention is not intended to be limiting.

What is claimed is:

1. A ureteral stent comprising:
a distal region comprising a tubular body defining a longitudinal axis and at least one lumen, and the distal region including a distal retention structure for maintaining a position of the ureteral stent with respect to a kidney; and
a proximal region in fluid communication with the distal region and comprising:
   a distal portion in communication with the distal region;
   a pliable portion in communication with the distal portion and disposable within a ureteral orifice, the pliable portion compressible upon the exertion of a pressure by the ureteral orifice, the pliable portion includes a section that is softer than the distal portion and the distal region; and
   a proximal portion in communication with the pliable portion and comprising at one or more flexible filaments forming at least one loop, the filaments having a length sufficient to remain within a bladder when the distal retention structure is positioned within the kidney.

2. The ureteral stent of claim 1 wherein the at least one loop has a retention force insufficient to maintain the ureteral stent within the bladder.

3. The ureteral stent of claim 1 wherein the pliable portion extends distally from the ureteral orifice about 3 centimeters or more.

4. The ureteral stent of claim 1 wherein the pliable portion comprises a distal end of the one or more filaments.

5. The ureteral stent of claim 1 wherein, upon exertion of the pressure, the pliable portion collapses sufficiently to inhibit urine reflux.

6. The ureteral stent of claim 1 wherein the one or more filaments are sufficiently resilient to provide drainage along an interstitial space between the filaments.

7. The ureteral stent of claim 6 wherein the interstitial space is at least partially collapsible upon exertion of body pressure.

8. The ureteral stent of claim 1 wherein the at least one loop is formed from one continuous filament.

9. The ureteral stent of claim 1 comprising at least two loops, each loop formed from one continuous filament.

10. The ureteral stent of claim 9 wherein the pliable portion comprises a distal end of the filaments, the filaments configured to minimize any sharp exterior edges at a junction of the distal portion.

11. The ureteral stent of claim 1 wherein the proximal region is integrally formed with the distal region.

12. The ureteral stent of claim 1 wherein the distal region has a hardness greater than the proximal region.

13. The ureteral stent of claim 12 wherein the hardness of the ureteral stent gradually decreases from a distal location of the distal region to a proximal location of the proximal region.

14. The ureteral stent of claim 1 wherein the proximal region has a hardness of about 60-80 Shore A.

15. The ureteral stent of claim 1 wherein the distal region has a hardness of at least about 80-110 Shore A.

16. The ureteral stent of claim 1 wherein a length of the loop is sufficient to maintain at least a portion of the loop within the bladder after intubation, including upon routine movement of the kidney and the bladder.

17. The ureteral stent of claim 1 wherein the one or more filaments have sufficient tensile strength to provide for extubation of the stent via the bladder.

18. The ureteral stent of claim 1 further comprising a lubricious coating.

19. The ureteral stent of claim 1 further comprising one or more openings disposed along the tubular body.

20. A ureteral stent comprising:
a distal region comprising a tubular body defining a longitudinal axis and at least one lumen, and the distal region including a distal retention structure for maintaining a position of the ureteral stent with respect to a kidney; and
a proximal region in fluid communication with the distal region and comprising:
   a distal portion in communication with the distal region;
   a pliable portion in communication with the distal portion and disposable within a ureteral orifice, the pliable portion compressible upon the exertion of a pressure by the ureteral orifice; and
   a proximal portion in communication with the pliable portion and comprising at least two loops, each of the at least two loops being formed from one continuous filament, the filaments having a length sufficient to remain within a bladder when the distal retention structure is positioned within the kidney.

21. A ureteral stent comprising:
a distal region comprising a tubular body defining a longitudinal axis and at least one lumen, and the distal region including a distal retention structure for maintaining a position of the ureteral stent with respect to a kidney; and
a proximal region in fluid communication with the distal region and comprising:
   a distal portion in communication with the distal region;
   a pliable portion in communication with the distal portion and disposable within a ureteral orifice, the pliable portion compressible upon the exertion of a pressure by the ureteral orifice; and
   a proximal portion in communication with the pliable portion and comprising at one or more flexible filaments forming at least one loop, the filaments having a length sufficient to remain within a bladder when the distal retention structure is positioned within the kidney,
the distal region having a hardness greater than a hardness of the proximal region.

* * * * *